,

US008741557B2

(12) United States Patent
Strom et al.

(10) Patent No.: US 8,741,557 B2
(45) Date of Patent: Jun. 3, 2014

(54) PREDICTING GRAFT REJECTION

(75) Inventors: Terry B. Strom, Brookline, MA (US); Towia Libermann, Chestnut Hill, MA (US); Asher Schachter, Needham, MA (US)

(73) Assignees: Beth Israel Deaconess Medical Center, Inc., Boston, MA (US); Children's Medical Center Corporation, Boston, MA (US)

( * ) Notice: Subject to any disclaimer, the term of this patent is extended or adjusted under 35 U.S.C. 154(b) by 1304 days.

(21) Appl. No.: 10/545,198

(22) PCT Filed: Feb. 17, 2004

(86) PCT No.: PCT/US2004/004839
§ 371 (c)(1),
(2), (4) Date: Jul. 6, 2006

(87) PCT Pub. No.: WO2004/074815
PCT Pub. Date: Sep. 2, 2004

(65) Prior Publication Data
US 2007/0122806 A1    May 31, 2007

Related U.S. Application Data

(60) Provisional application No. 60/447,540, filed on Feb. 14, 2003.

(51) Int. Cl.
*C12Q 1/68* (2006.01)

(52) U.S. Cl.
USPC ......... 435/6.1; 435/6.12; 435/68.1; 435/70.1; 435/325

(58) Field of Classification Search
USPC ........ 435/6.1, 6.12, 91.2, 174, 283.1; 422/50, 422/417, 420, 68.1, 69, 500, 131, 138
See application file for complete search history.

(56) References Cited

U.S. PATENT DOCUMENTS

| 6,355,775 B1 | 3/2002 | Nagasawa et al. |
| 2002/0132235 A1 | 9/2002 | Avihingsanon et al. |
| 2002/0142461 A1 | 10/2002 | Ni et al. |
| 2002/0151009 A1 | 10/2002 | Ni et al. |

FOREIGN PATENT DOCUMENTS

| EP | 0 379 904 A | 8/1990 |
| WO | WO 99/55859 A2 | 11/1999 |
| WO | 01/81916 | 11/2001 |
| WO | WO 0181916 A2 * | 11/2001 |

OTHER PUBLICATIONS

Wiggins eta l., "Tumour necrosis factor levels during acute rejection and acute tubular necrosis in renal transplant recipients," Transplant Immunology, 2000, vol. 8, pp. 211-215.*
Abdallah et al., "Evaluation of plasma levels of tumour necrosis factor alpha and interleukin-6 as rejection markers in a cohort of 142 heart-grafted patients followed by endomyocardial biopsy," European Heart Journal, 1997, vol. 18, pp. 1024-1029.*
Dragun et al., "ICAM-1 antisense oligodesoxynucleotides prevent reperfusion injury and enhance immediate graft function in renal transplantation," Kidney International, 1998, vol. 54, pp. 590-602.*
McDiarmid et al., "The correlation of intragraft cytokine expression with rejection in rat small intestine transplantation," Transplantation, Sep. 1994, vol. 58, No. 6, pp. 690-697.*
Pavlakis et al., "Intragraft IL-15 Transcripts are Increased in Human Renal Allograft Rejection," Transplantation, Aug. 1996, vol. 62, No. 4, print out pp. 1-10.*
McLaughlin et al., "Evaluation of Sequential Plasma and Urinary Tumor Necrosis Factor Alpha Levels in Renal Allograft Recipients", *Transplantation*, vol. 51., No. 6, Jun. 1991, pp. 1225-1229.
Communication dated Feb. 26, 2009 received in related European Appln. No. 04 711 942.5.
European Patent Office Supplementary Search Report; Application No. 04711942.5-2402; Oct. 6, 2006; pp. 1-5.
European Communication; Application No. 04711942.5-2402; Jun. 15, 2007; pp. 1-7.
Australian Office Action; Application No. 2004213839; Oct. 27, 2008; pp. 1-4.
Canadian Office Action; Application No. 2,516,013; Dec. 7, 2011; pp. 1-4.
European Office Action; Application No. 04711942.5-2402; mailed Apr. 24, 2012; Applicant: Beth Israel Deaconess Medical Center, Inc.; pp. 1-3.
Canadian Office Action; Application No. 2,516,013; mailed Jan. 16, 2013; Applicant: Beth Israel Deaconess Medical Center, Inc., Children's Medical Center Corporation; 2 pages.
Written Opinion; Application No. PCT/US04/04839; mailed Oct. 13, 2004; Applicant: Beth Israel Deaconess Medical Center, Inc., 7 pages.

* cited by examiner

*Primary Examiner* — Ardin Marschel
(74) *Attorney, Agent, or Firm* — Fish & Richardson P.C.

(57) ABSTRACT

Prognostic methods useful in assessing patients who have received a transplant and reagents that can be used to carry out those methods are provided. The inventions are based, in part, on our analysis of gene expression in renal allografts and clinical parameters, i.e., variables associated with the donor, the recipient and/or the graft. The genes that can be assessed include those encoding agents that mediate inflammation, immune activation, and cell death (we may refer to these genes as "inflammatory", "immune" or "cytoprotective"). Surprisingly, the levels of gene expression could predict the occurrence of DGF, AR, and the quality of later graft function even when analyzed shortly after (e.g., after vascular anastomosis and tissue reperfusion). We also found that clinical parameters available at the time of transplantation correlate with decreased graft health and can be considered in combination with gene expression to evaluate a patient's risk for an adverse outcome.

25 Claims, 13 Drawing Sheets

| Variable | DGF P value | DGF R² | DGF Direction | AR P value | AR R² | AR Direction | 6-Month Function P value | 6-Month Function R² | 6-Month Function Direction |
|---|---|---|---|---|---|---|---|---|---|
| age | NS | | | NS | | | NS | | |
| recipient race | NS | | | NS | | | 0.023 | 0.09 | AA |
| transplant number | NS | | | NS | | | NS | | |
| donor type | <0.001 | 0.15 | CAD | 0.042 | 0.01 | CAD | 0.002 | 0.15 | CAD |
| induction | NS | | | NS | | | NS | | |
| donor age | NS | | | NS | | | 0.012 | 0.11 | Up |
| donor race | NS | | | NS | | | NS | | |
| CIT | 0.005 | 0.27 | Up | NS | | | NS | | |
| WIT | 0.013 | 0.20 | Up | NS | | | NS | | |
| DGF | N/A | N/A | | 0.007 | 0.24 | Up | NS | | |
| AR | N/A | N/A | | 0.003 | 0.11 | DGF | NS | | |
| HLA match | NS | | | NS | | | 0.005 | 0.56 | AR |
| TNFα | <0.001 | 0.69 | Up | 0.028 | 0.07 | Up | 0.005 | 0.19 | Down |
| CD25 | <0.001 | 0.19 | Up | <0.001 | 0.22 | Up | NS | | |
| TGFβ | <0.001 | 0.34 | Up | 0.007 | 0.11 | Up | 0.004 | 0.15 | Up |
| A20 | <0.001 | 0.12 | Up | NS | | | NS | | |
| BclXl | NS | | | NS | | | NS | | |
| Bcl2 | NS | | | NS | | | 0.040 | 0.07 | Down |
| IL10 | <0.001 | 0.22 | Up | NS | | | NS | | |
| IL6 | NS | | | 0.016 | 0.08 | Up | NS | | |
| PECAM | NS | | | NS | | | NS | | |
| ICAM | 0.006 | 0.10 | Up | 0.049 | 0.06 | Up | NS | | |
| NFκB | NS | | | NS | | | NS | | |
| HO1 | NS | | | 0.023 | 0.07 | Up | NS | | |
| CD40 | NS | | | NS | | | NS | | |
| rRNA | NS | | | <0.001 | 0.19 | Up | NS | | |
| CD3 | NS | | | NS | | | NS | | |
| IFNγ | NS | | | NS | | | NS | | |

| Multivariate model significant variables from above | R² 0.98 | | | R² 0.88 | | | R² 0.48 WITH AR / 0.48 WITHOUT AR | | |

| ANN ROC AUC | ROC AUC | | | ROC AUC | | | ROC AUC | | |
| clinical + genes* | 1.00 | | | 0.73 | | | 0.84 | | |
| clinical only* | 1.00 | | | 0.56 | | | 0.72 | | |
| genes only* | 0.87 | | | 0.77 | | | 0.78 | | |

* Clinical and/or gene variables deemed statistically significant by logistic regression.
AR was not included as a clinical variable in the 6-month function models.

FIG. 1

FIG. 5A 26S proteasome-associated pad1 homolog
3'-phosphoadenosine 5'-phosphosulfate synthase 1
4-hydroxyphenylpyruvate dioxygenase
5-methyltetrahydrofolate-homocysteine methyltransferase
6-phosphofructo-2-kinase/fructose-2,6-biphosphatase 3
6-pyruvoyltetrahydropterin synthase
a disintegrin and metalloproteinase domain 10
acetyl-Coenzyme A acyltransferase 1 (peroxisomal 3-oxoacyl-Coenzyme A thiolase)
acid phosphatase 5, tartrate resistant
actin related protein 2/3 complex, subunit 1A (41 kD)
actin related protein 2/3 complex, subunit 1B (41 kD)
actin related protein 2/3 complex, subunit 2 (34 kD)
actin related protein 2/3 complex, subunit 5 (16 kD)
actin, beta
actinin, alpha 1
acyl-Coenzyme A dehydrogenase, C-2 to C-3 short chain
adaptor-related protein complex 2, sigma 1 subunit
ADP-ribosylation factor 4
afamin
alanine-glyoxylate aminotransferase (oxalosis I; hyperoxaluria I; glycolicaciduria; serine-pyruvate aminotransferase)
aldehyde dehydrogenase 1 family, member A1
aldehyde dehydrogenase 3 family, member A2
aldo-keto reductase family 1, member A1 (aldehyde reductase)
aldolase B, fructose-bisphosphate
alpha one globin (HBA1)
alpha-2-glycoprotein 1, zinc
amiloride binding protein 1 (amine oxidase (copper-containing))
amino acid transporter 2
aminoacylase 1
aminolevulinate, delta-, synthase 1
amyloid beta (A4) precursor-like protein 2
anaphase-promoting complex subunit 10
ankyrin 2, neuronal
annexin A11
annexin A2
annexin A5
antigen identified by monoclonal antibodies 12E7, F21 and O13
apolipoprotein E
apolipoprotein H (beta-2-glycoprotein I)
apolipoprotein M
arachidonate 5-lipoxygenase
argininosuccinate synthetase (ASS)
ARP2 actin-related protein 2 homolog (yeast)
arsA arsenite transporter, ATP-binding, homolog 1 (bacterial)
asparagine synthetase
ATP binding protein associated with cell differentiation
ATP citrate lyase
ATPase, Ca++ transporting, cardiac muscle, slow twitch 2
ATPase, Na+/K+ transporting, alpha 1 polypeptide
B-cell CLL/lymphoma 6 (zinc finger protein 51)
B-cell linker
B-cell translocation gene 1, anti-proliferative
beta globin chain variant (HBB)

FIG. 5B beta-2-microglobulin
betaine-homocysteine methyltransferase
beta-tubulin
B-factor, properdin (BF)
biphenyl hydrolase-like (serine hydrolase; breast epithelial mucin-associated antigen)
bromodomain-containing 2
calnexin
calpain, small subunit 1
calpastatin
calumenin
capping protein (actin filament), gelsolin-like
carbohydrate (N-acetylglucosamine 6-O) sulfotransferase 6
carbonyl reductase
carboxylesterase 2 (intestine, liver)
casein kinase 1, delta
CASP8 and FADD-like apoptosis regulator
catenin (cadherin-associated protein), alpha 1 (102kD)
cathepsin F
CD14 antigen
CD14 antigen
CD151 antigen
CD163 antigen
CD24 antigen (small cell lung carcinoma cluster 4 antigen)
CD24 antigen (small cell lung carcinoma cluster 4 antigen)
CD59 antigen p18-20 (antigen identified by monoclonal antibodies 16.3A5, EJ16, EJ30, EL32 and G344)
CD59 antigen p18-20 (antigen identified by monoclonal antibodies 16.3A5, EJ16, EJ30, EL32 and G344)
CD59 antigen p18-20 (antigen identified by monoclonal antibodies 16.3A5, EJ16, EJ30, EL32 and G344)
CGI-100 protein
CGI-146 protein
CGI-36 protein
CGI-86 protein
chitobiase, di-N-acetyl-
chloride channel ABP
chloride intracellular channel 5
chromosome 1 open reading frame 27
claudin 3
clusterin (complement lysis inhibitor, SP-40,40, sulfated glycoprotein 2, testosterone-repressed prostate message 2, apolipoprotein J)
clusterin (complement lysis inhibitor, SP-40,40, sulfated glycoprotein 2, testosterone-repressed prostate message 2, apolipoprotein J)
collagen, type I, alpha 2
complement component 1, s subcomponent
craniofacial development protein 1
crystallin, alpha B
crystallin, mu
cubilin (intrinsic factor-cobalamin receptor)
cutaneous T-cell lymphoma-associated tumor antigen se20-4; differentially expressed nucleolar TGF-beta1 target protein (DENTT)
cyclin-dependent kinase (CDC2-like) 10
cystatin B (stefin B)
cysteine and glycine-rich protein 2
cysteine and glycine-rich protein 2
cytochrome P450, subfamily I (dioxin-inducible), polypeptide 1 (glaucoma 3, primary infantile)
cytochrome P450, subfamily IIB (phenobarbital-inducible), polypeptide 6 (CYP2B6)

FIG. 5C cytochrome P450, subfamily IVA, polypeptide 11
cytochrome P450, subfamily IVF, polypeptide 3 (leukotriene B4 omega hydroxylase)
cytochrome P450, subfamily XXVIIA (steroid 27-hydroxylase, cerebrotendinous xanthomatosis), polypeptide 1 (CYP27A1)
cytoskeleton-associated protein 1
cytosolic acyl coenzyme A thioester hydrolase
D-amino-acid oxidase (DAO)
DEAD/H (Asp-Glu-Ala-Asp/His) box polypeptide 15
defender against cell death 1
deiodinase, iodothyronine, type I
deleted in lymphocytic leukemia, 1
DEME-6 protein
dihydrolipoamide branched chain transacylase (E2 component of branched chain keto acid dehydrogenase complex; maple syrup urine disease)
dipeptidase 1 (renal)
discoidin domain receptor family, member 1
discoidin domain receptor family, member 1
DKFZP434D156 protein
DKFZP564D116 protein
DKFZP586B0923 protein
dolichyl-diphosphooligosaccharide-protein glycosyltransferase
dopa decarboxylase (aromatic L-amino acid decarboxylase)
dynamin 2
early development regulator 2 (polyhomeotic 2 homolog)
ectonucleotide pyrophosphatase/phosphodiesterase 4 (putative function)
endothelin receptor type B
enoyl Coenzyme A hydratase, short chain, 1, mitochondrial
eukaryotic translation elongation factor 1 epsilon 1
eukaryotic translation initiation factor 2, subunit 2 (beta, 38kD )
eukaryotic translation initiation factor 2-alpha kinase 3
eukaryotic translation initiation factor 4 gamma, 1
exportin 1 (CRM1 homolog, yeast)
fatty acid binding protein 1, liver
fatty-acid-Coenzyme A ligase, very long-chain 1
fer-1-like 3, myoferlin (C. elegans)
fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome)
fibronectin 1
flavin containing monooxygenase 1
flotillin 1
folate receptor 1 (adult)
formiminotransferase cyclodeaminase
fructose-1,6-bisphosphatase
fucosyltransferase 6 (alpha (1,3) fucosyltransferase)
fucosyltransferase 6 (alpha (1,3) fucosyltransferase)
FYN oncogene related to SRC, FGR, YES
G1 to S phase transition 1
GABA(A) receptor-associated protein like 1
galactosidase, beta 1
glioma tumor suppressor candidate region gene 2
glucose phosphate isomerase
glutamine-fructose-6-phosphate transaminase 1
glutaryl-Coenzyme A dehydrogenase

FIG. 5D glyceraldehyde-3-phosphate dehydrogenase
glycine-N-acyltransferase
glycogenin
glyoxylate reductase/hydroxypyruvate reductase
GNAS complex locus
growth factor receptor-bound protein 14
GTP cyclohydrolase I feedback regulatory protein
guanine nucleotide binding protein (G protein), alpha inhibiting activity polypeptide 3
guanine nucleotide binding protein (G protein), beta polypeptide 1
H1 histone family, member 0
H1 histone family, member 2
heat shock 27kD protein 1
hematological and neurological expressed 1
hemoglobin, alpha 1 (HBA1)
hemoglobin, alpha 2
hemoglobin, beta
heterogeneous nuclear ribonucleoprotein D-like
heterogeneous nuclear ribonucleoprotein H3 (2H9)
heterogeneous nuclear ribonucleoprotein M
hexabrachion (tenascin C, cytotactin)
hexokinase 1
HIF-1 responsive RTP801
high-mobility group (nonhistone chromosomal) protein 17-like 3
HIV-1 TAR RNA binding protein (TARBP-b)
HLA-B associated transcript 1
hydroxyacid oxidase 2 (long chain)
hydroxyprostaglandin dehydrogenase 15-(NAD)
hypothetical protein
hypothetical protein DKFZp434F0318
hypothetical protein DKFZp434K046
hypothetical protein FLJ10055
hypothetical protein FLJ10743
hypothetical protein FLJ12089
hypothetical protein FLJ12151
hypothetical protein FLJ12666
hypothetical protein FLJ14054
hypothetical protein FLJ14153
hypothetical protein FLJ14972
hypothetical protein FLJ14972
hypothetical protein FLJ20075
hypothetical protein FLJ20208
hypothetical protein FLJ20406
hypothetical protein FLJ20477
hypothetical protein FLJ20699
hypothetical protein FLJ20898
hypothetical protein FLJ20920
hypothetical protein FLJ21047
hypothetical protein FLJ21313
hypothetical protein FLJ21634
hypothetical protein FLJ21736
hypothetical protein FLJ22756
hypothetical protein MGC11242
hypothetical protein MGC3279 similar to collectins

FIG. 5E hypothetical protein MGC4171
hypothetical protein PP3501
hypothetical protein PRO1068
hypothetical protein, estradiol-induced
hypothetical protein, similar to (U06944) PRAJA1
hypoxanthine phosphoribosyltransferase 1 (Lesch-Nyhan syndrome)
hypoxia-inducible factor 1, alpha subunit (basic helix-loop-helix transcription factor)
hypoxia-inducible factor 1, alpha subunit (basic helix-loop-helix transcription factor)
insulin induced gene 1
insulin receptor
integral type I protein
interferon induced transmembrane protein 1 (9-27)
interferon induced transmembrane protein 2 (1-8D)
interferon, gamma-inducible protein 16
interferon, gamma-inducible protein 16
interferon-stimulated transcription factor 3, gamma (48kD)
isopentenyl-diphosphate delta isomerase
isopentenyl-diphosphate delta isomerase
Janus kinase 1 (a protein tyrosine kinase)
jun D proto-oncogene
KDEL (Lys-Asp-Glu-Leu) endoplasmic reticulum protein retention receptor 2
keratin 18
keratin 19
keratin 8
ketohexokinase (fructokinase)
KIAA0103 gene product
KIAA0111 gene product
KIAA0193 gene product
KIAA0368 protein
KIAA0446 gene product
KIAA0790 protein
kynurenine 3-monooxygenase (kynurenine 3-hydroxylase)
L-3-hydroxyacyl-Coenzyme A dehydrogenase, short chain
lactate dehydrogenase A
LanC lantibiotic synthetase component C-like 1 (bacterial)
lectin, galactoside-binding, soluble, 1 (galectin 1)
lectin, galactoside-binding, soluble, 2 (galectin 2)
lipase A, lysosomal acid, cholesterol esterase (Wolman disease)
lipase protein
lipin 2
lipoma HMGIC fusion partner
loss of heterozygosity, 11, chromosomal region 2, gene A
LPS-induced TNF-alpha factor
LPS-induced TNF-alpha factor
LPS-induced TNF-alpha factor
LRP16 protein
lysosomal-associated membrane protein 1
lysyl oxidase-like 1
matrilin 2
matrin 3
matrix Gla protein
melanoma antigen, family D, 2
membrane interacting protein of RGS16

FIG. 5F membrane metallo-endopeptidase (neutral endopeptidase, enkephalinase, CALLA, CD10)
mercaptopyruvate sulfurtransferase
methionine sulfoxide reductase A
methionyl aminopeptidase 2
methyl-CpG binding domain protein 2
MHC class II HLA-DRA
microtubule-actin crosslinking factor 1
microtubule-associated protein tau
microtubule-associated protein, RP/EB family, member 1
microtubule-associated proteins 1A/1B light chain 3
midline 1 (Opitz/BBB syndrome)
mitochondrial ribosomal protein L15
mitochondrial ribosomal protein S12
mitofusin 1
mitogen-activated protein kinase kinase 3
mucin 1, transmembrane
mucin and cadherin-like (MUCDHL)
muscleblind-like (Drosophila)
myelin basic protein
myosin, heavy polypeptide 9, non-muscle
NAD(P)H dehydrogenase, quinone 1
NAD(P)H dehydrogenase, quinone 2
NADH dehydrogenase (ubiquinone) Fe-S protein 1 (75kD) (NADH-coenzyme Q reductase)
nardilysin (N-arginine dibasic convertase)
natriuretic peptide receptor C/guanylate cyclase C (atrionatriuretic peptide receptor C)
natural killer-tumor recognition sequence
N-ethylmaleimide-sensitive factor
nicotinamide N-methyltransferase
non-metastatic cells 1, protein (NM23A) expressed in
novel MAFF (v-maf musculoaponeurotic fibrosarcoma (avian) oncogene family, protein F) LIKE protein
novel RGD-containing protein
NPD009 protein
NS1-associated protein 1
nuclear receptor subfamily 1, group I, member 3
nuclear receptor subfamily 4, group A, member 3
nucleolar protein family A, member 3 (HACA small nucleolar RNPs) (NOLA3)
O-6-methylguanine-DNA methyltransferase
oxysterol binding protein-like 11
p8 protein (candidate of metastasis 1)
palladin
parathyroid hormone receptor 1
PEF protein with a long N-terminal hydrophobic domain (peflin)
peptidylprolyl isomerase C (cyclophilin C)
peptidylprolyl isomerase F (cyclophilin F)
peroxiredoxin 4
peroxisomal short-chain alcohol dehydrogenase
phenylalanine hydroxylase
phosphatidic acid phosphatase type 2B
phosphodiesterase 4C, cAMP-specific (phosphodiesterase E1 dunce homolog, Drosophila)
phosphoenolpyruvate carboxykinase 1 (soluble)
phosphoenolpyruvate carboxykinase 2 (mitochondrial)
phosphofructokinase, platelet
phosphoglycerate kinase 1

FIG. 5G phospholipid scramblase 1
phosphorylase, glycogen; brain
phosphoserine phosphatase
phytanoyl-CoA hydroxylase (Refsum disease)
potassium inwardly-rectifying channel, subfamily J, member 15
pre-B-cell colony-enhancing factor
procollagen-proline, 2-oxoglutarate 4-dioxygenase (proline 4-hydroxylase), alpha polypeptide II
procollagen-proline, 2-oxoglutarate 4-dioxygenase (proline 4-hydroxylase), beta polypeptide (protein disulfide isomerase; thyroid hormone binding protein p55)
progesterone receptor membrane component 1
proline dehydrogenase (oxidase) 2
prominin-like 1 (mouse)
proteasome (prosome, macropain) 26S subunit, ATPase, 3
proteasome (prosome, macropain) activator subunit 1 (PA28 alpha)
proteasome (prosome, macropain) subunit, alpha type, 1
proteasome (prosome, macropain) subunit, beta type, 10
proteasome (prosome, macropain) subunit, beta type, 4
protein kinase C binding protein 1
protein kinase C, mu
protein kinase, cAMP-dependent, regulatory, type I, alpha (tissue specific extinguisher 1)
protein phosphatase 1, regulatory (inhibitor) subunit 3C
protein tyrosine phosphatase type IVA, member 2
protein tyrosine phosphatase, non-receptor type 12
protein tyrosine phosphatase, receptor type, F
proteoglycan 1, secretory granule
Purkinje cell protein 4
putative N-acetyltransferase Camello 2
putative nuclear protein
Putative prostate cancer tumor suppressor
pyruvate carboxylase
pyruvate dehydrogenase (lipoamide) alpha 1
pyruvate dehydrogenase kinase, isoenzyme 2
pyruvate kinase, muscle
quinolinate phosphoribosyltransferase (nicotinate-nucleotide pyrophosphorylase (carboxylating))
RAB11A, member RAS oncogene family
RAB31, member RAS oncogene family
RAB7, member RAS oncogene family-like 1
RAN binding protein 7
regulator of G-protein signalling 2, 24kD
renin binding protein
retinoblastoma binding protein 8
retinol binding protein 4, plasma
Rho GTPase activating protein 8
Rho-associated, coiled-coil containing protein kinase 2
ribophorin II
ring-box 1
RNA binding motif protein 3
RNA binding motif protein 9
RNA binding motif, single stranded interacting protein 1
RNA-binding protein gene with multiple splicing
rTS beta protein
S100 calcium binding protein A11 (calgizzarin)
S100 calcium binding protein A13

FIG. 5H

S100 calcium binding protein A8 (calgranulin A)
S100 calcium binding protein A8 (calgranulin A)
S-adenosylhomocysteine hydrolase
S-adenosylhomocysteine hydrolase-like 1
sarcosine oxidase
selenoprotein P, plasma, 1
selenoprotein T
selenoprotein X, 1
sema domain, immunoglobulin domain (Ig), short basic domain, secreted, (semaphorin) 3B
sema domain, immunoglobulin domain (Ig), transmembrane domain (TM) and short cytoplasmic domain, (semaphorin) 4D
serine (or cysteine) proteinase inhibitor, clade A (alpha-1 antiproteinase, antitrypsin), member 1
serine (or cysteine) proteinase inhibitor, clade A (alpha-1 antiproteinase, antitrypsin), member 6
serine (or cysteine) proteinase inhibitor, clade G (C1 inhibitor), member 1, (angioedema, hereditary)
serine/threonine kinase 24 (STE20 homolog, yeast)
serologically defined breast cancer antigen NY-BR-20
SH3-domain GRB2-like endophilin B1
Siah-interacting protein
signal sequence receptor, delta (translocon-associated protein delta)
signal transducer and activator of transcription 1, 91kD
signal transducer and activator of transcription 3 (acute-phase response factor)
similar to S. cerevisiae RER1
single Ig IL-1R-related molecule
small nuclear ribonucleoprotein polypeptide A'
SMT3 suppressor of mif two 3 homolog 2 (yeast)
solute carrier family 10 (sodium/bile acid cotransporter family), member 2
solute carrier family 12 (sodium/chloride transporters), member 3
solute carrier family 16 (monocarboxylic acid transporters), member 5
solute carrier family 2 (facilitated glucose/fructose transporter), member 5
solute carrier family 22 (organic anion transporter), member 6
solute carrier family 22 (organic cation transporter), member 1-like
solute carrier family 25 (mitochondrial carrier; dicarboxylate transporter), member 10
solute carrier family 28 (sodium-coupled nucleoside transporter), member 1
solute carrier family 34 (sodium phosphate), member 1
solute carrier family 6 (neurotransmitter transporter, GABA), member 13
solute carrier family 7 (cationic amino acid transporter, y+ system), member 7
sorbitol dehydrogenase
sorcin
splicing factor, arginine/serine-rich 2
splicing factor, arginine/serine-rich 2
splicing factor, arginine/serine-rich 3
SRY (sex determining region Y)-box 4
staufen, RNA binding protein (Drosophila)
steroid dehydrogenase homolog
sulfotransferase family, cytosolic, 1C, member 1
suppression of tumorigenicity 14 (colon carcinoma, matriptase, epithin)
suppression of tumorigenicity 5
synaptic nuclei expressed gene 2
TAP binding protein (tapasin)
tetraspan 3
thioredoxin interacting protein
thiosulfate sulfurtransferase (rhodanese)
thymosin, beta 10

FIG. 5I thymosin, beta 4-like
thyroid hormone receptor interactor 12
tissue inhibitor of metalloproteinase 1 (erythroid potentiating activity, collagenase inhibitor)
tissue inhibitor of metalloproteinase 3 (Sorsby fundus dystrophy, pseudoinflammatory)
tousled-like kinase 1
TPA regulated locus
transforming growth factor, beta-induced, 68kD
transgelin 2
transglutaminase 2 (C polypeptide, protein-glutamine-gamma-glutamyltransferase)
transketolase (Wernicke-Korsakoff syndrome)
translocase of inner mitochondrial membrane 13 homolog B (yeast)
translocating chain-associating membrane protein
transmembrane 9 superfamily member 2
transmembrane trafficking protein
TRK-fused gene
tropomyosin 1 (alpha)
tryptophanyl-tRNA synthetase
tubulin alpha 6
tubulin, alpha, ubiquitous
tumor differentially expressed 1
tumor necrosis factor, alpha-induced protein 1 (endothelial)
tumor protein D52
tumor protein D52-like 1
tumor-associated calcium signal transducer 2
two-pore channel 1, homolog
tyrosine 3-monooxygenase/tryptophan 5-monooxygenase activation protein, zeta polypeptide
ubiquitin specific protease 24
ubiquitin-conjugating enzyme E2D 3 (UBC4/5 homolog, yeast)
UBX domain-containing 2
UDP glycosyltransferase 1 family, polypeptide A1
UDP glycosyltransferase 1 family, polypeptide A6
UDP glycosyltransferase 1 family, polypeptide A9
uncharacterized hematopoietic stem/progenitor cells protein MDS030
ureidopropionase, beta
valosin-containing protein
vascular Rab-GAP/TBC-containing
vesicle docking protein p115
villin 2 (ezrin)
vimentin
vitamin A responsive; cytoskeleton related
vitamin D (1,25- dihydroxyvitamin D3) receptor
v-maf musculoaponeurotic fibrosarcoma oncogene homolog (avian)
WAP four-disulfide core domain 2
WW domain binding protein 11
X-prolyl aminopeptidase (aminopeptidase P) 2, membrane-bound
zinc finger protein 103 homolog (mouse)
zinc finger protein 161
zinc finger protein 207

PREDICTING GRAFT REJECTION

CROSS-REFERENCE TO RELATED APPLICATIONS

This application claims the benefit of priority of U.S. Ser. No. 60/447,540, filed Feb. 14, 2003, the contents of which is hereby incorporated by reference in its entirety.

TECHNICAL FIELD

This invention relates to organ transplantation and, more particularly, to compositions and methods for predicting graft rejection and treating transplant recipients.

BACKGROUND

Complications often occur following organ transplantation that can impair long-term graft function. For example, in the event the transplanted organ is a kidney, the recipient can experience chronic allograft nephropathy. With severe complications, the graft can fail entirely (see, e.g., Shoskes and Cecka, *Transplantation* 66:1697-1701, 1998; Matas et al., *Transplantation* 69:54-58, 2000; Terasaki et at, *N. Engl. J. Med.* 333:333-336, 1995; Halloran and Aprile, *Transplantation* 45:122-127, 1988; and Ojo et al, *Transplantation* 63:757-758, 1997). Presently, while the probability that a randomly selected transplant recipient will experience delayed graft function (DGF) or acute rejection (AR) is fairly low, there is no timely and refined means to accurately predict the outcome and thereby identify such patients. The quality of the allograft at the time of engraftment (the so-called "zero-hour") influences clinical outcome, but conventional histological evaluation of donor tissue does not provide a means to predict clinical outcomes (Curschellas et al, *Clin. Nephrol.* 36:215-222, 1991). Similarly, catastrophic events, such as donor brain death and donor organ "cold ischemia time" appear to influence the rate of DGF, but these factors are not adequate predictors of long-term graft function in individual patients (Prommool et al, *Am. Soc. Nephrol.* 11:565-573, 2000).

SUMMARY

The work described here provides materials and means to identify patients at risk for DGF, AR, or more tissue-specific conditions such as chronic allograft nephropathy (or chronic rejection of any tissue type). As such, the compositions and methods of the invention can impact the way transplant recipients are treated (before, during, and/or after a transplantation procedure). For example, patients identified as having a high risk of DGF, AR, or another undesirable clinical outcome (e.g., a poor long-term prognosis) can be treated more aggressively with, for example, immunosuppressants or other therapeutic agents. To the contrary, patients identified as "low risk" may be treated less aggressively (e.g., with minimal immunosuppressants) and thereby avoid the side effects commonly associated with immunosuppression or other therapies.

To assess patient risk, we developed surrogate markers for graft function and applied them soon after vascular reperfusion. More specifically, we performed transcriptional analysis of renal allografts for inflammatory or pro-inflammatory, immune activation, anti-apoptotic or cytoprotective, and other types of genes shortly after the completion of vascular anastomosis. Accordingly, the invention features methods of evaluating graft rejection by assessing gene expression in a graft at the time it is transplanted into a host; at the time of, or soon after, vascular anastomosis; at the time of, or soon after, vascular reperfusion; or around the time of any process that is considered to occur at the "zero hour". In many cases, a number of these events will coincide, but in other cases, they can be temporally distinct. For example, some transplanted organs are reperfused at the time they are connected to the host's circulation (and this connection occurs at the time the organ is transplanted into the host). In other cases (e.g., where the transplant includes transplanted cells, such as islet cells), reperfusion may not occur for days or weeks following transplantation. Thus, while the methods of the invention can be carried out with samples obtained during the operation in which the graft was transplanted, they can also be carried out with samples subsequently obtained. While there may be advantages to assessing patient risk as soon after transplantation as possible, the invention is not so limited; the materials and methods described below can be employed at any time (e.g., hours, days, weeks, or months) following transplantation (or following one of the events described above (e.g., following reperfusion)). The materials and methods of the invention can also be employed more than once. For example, a surrogate marker (or a combination thereof) can be assessed within a biological sample obtained at the time of transplantation and at a subsequent time; at the time of reperfusion and at a subsequent time; etc. . . . .

In one embodiment, the invention features a method of predicting whether a host will experience delayed graft function, acute rejection, or another undesirable clinical outcome by (a) providing a sample that includes cells of the transplanted organ or tissue, and/or a bodily fluid in communication with that organ or tissue, shortly after vascular reperfusion (e.g., about 5, 10, 15, 20, or 30 minutes after reperfusion or about 1, 2, 3, 4, 5, 8, 10, 12, 16, 18, 20, or 24 hours after reperfusion) of the transplanted organ, or tissue and (b) determining the level of expression of one or more genes in the sample (the amount or relative amount of protein encoded by the gene is one indication of the level of gene expression; others are described below). While the gene(s) assessed are described further below, we note here that the gene(s) can encode a protein involved in inflammation or immune activation or a cytoprotective gene (e.g., an anti-apoptotic protein) (but the invention is not so limited; any of the genes listed in the Tables provided herein can be assessed alone or in combination with any other gene(s)); generally, increased expression of pro-inflammatory or immune activation genes indicates that the patient will experience a poor outcome (and would therefore be a candidate for more aggressive treatment (e.g., more aggressive administration of immunosuppressants)), while increased expression of cytoprotective genes, including anti-apoptotic genes, indicates that the graft is likely to function well in the patient (and that aggressive immunosuppression may not be required). The converse in expression is also true: generally, decreased expression of pro-inflammatory or immune activation genes indicates that a patient will experience a good outcome (and that aggressive immunosuppression may not be required) and decreased expression of cytoprotective genes indicates that the patient will experience a poor outcome (requiring aggressive immunosuppression). As described further below, both types of genes can be assessed in the methods of the invention.

Thus, when the level of expression of certain genes (e.g., a pro-inflammatory (or inflammatory) or immune response-associated gene) is higher in a test sample (i.e., a sample obtained from a transplant recipient) than in (a) a control sample (e.g., an organ, tissue, or biological fluid obtained from a healthy donor (i.e., a patient who has not received a transplant)) or (b) a reference standard, the host is likely to suffer from DGF, AR, or some other undesirable clinical outcome. For example, elevated levels of CD25 and CD40 expression indicate that a host is likely to suffer from poor graft function; an elevation in other genes, such as A20 and Bcl-$X_L$, indicates that the host is unlikely to suffer from DGF, AR, or some other undesirable clinical outcome (and in that event, the host is likely to retain good graft function). One of ordinary skill in the art will recognize that some genes are expressed in a tissue-specific manner; genes that are not expressed in a transplanted tissue of interest will obviously not be ideal candidates for assessment.

We discovered not only that an elevation in pro-inflammatory gene expression predicts poor clinical outcome while an elevation in cytoprotective gene expression predicts a good clinical outcome, but also that assessing these types of genes in concert offers a powerful predictive tool. Accordingly, where two or more genes are assessed, one can be a pro-inflammatory gene (e.g., a gene encoding an inflammatory cytokine) and the other can be a cytoprotective gene. Elevation of the former and reduction of the later is, or can be, an even stronger predictor of poor clinical outcome than either observation alone. Thus, the methods of the invention include those in which one assesses the balance between immune or inflammatory gene products and anti-apoptotic gene products in order to predict clinical outcome (e.g., a transplant recipient's prognosis over the short or long term). One of ordinary skill in the art will recognize genes belonging to the relevant categories (e.g., pro-inflammatory, immune, and cytoprotective genes), and specific examples are given below.

The biological sample tested can be obtained after the transplanted organ or tissue is reperfused (e.g., at least or about 1, 2, 5, 10, 15, or 20 minutes after anastamosis or reperfusion) and up until the time the incision created to carry out the transplant is closed or the transplanted organ or tissue is no longer accessible to the surgeon. While it is possible to obtain the sample even after the transplantation procedure is complete, we expect this will most likely be done when reperfusion occurs a significant amount of time after the surgical procedure ends; thus, on some occasions, a patient may be subjected to a second procedure to obtain a sample containing a subset of the transplanted cells. Alternatively, or in addition, at any time following transplantation or reperfusion, a biological fluid in communication with the cells may be obtained and tested (e.g., fluids can be obtained during the initial surgical procedure; blood, urine, spinal fluid, or other biological fluid can also be obtained subsequently).

A gene of interest (which we may also refer to as a "surrogate marker"), or any combination thereof, can be assessed using any procedure that determines the level of RNA or protein expression or activity, many of which are presently known in the art (including a PCR-based assay (e.g., "real-time" PCR), which makes the results available quickly). Moreover, where more than one marker is assessed, the procedure(s) for detecting that marker can be carried out simultaneously (i.e., at or about the same time (e.g., within the hour or on the same day) or at different points in time (e.g., the next day or within the next week, month, or several months). For example, one can initially test the biological sample for expression of one or more inflammatory or immune markers (e.g., cytokines) and one or more cytoprotective markers. Alternatively, one or more markers within a first class of markers can be tested and, based upon the results obtained, one or more markers within a second class of markers can be tested subsequently.

Determining the status of a graft at (or around) the time of transplantation, provides an improvement over the measures presently available to predict subsequent (i.e., post-transplantation) clinical events. Rapid analysis of the molecular status of the graft at (or around) the time of reperfusion has provided (1) insight into the pathologic processes that endanger long-term graft function and (2) a basis for prescribing individualized treatments for graft recipients (the goal of the individualized treatment being to optimize, on a case-by-case basis, each patient's prognosis). The use of high-dose anti-rejection therapy, superimposed upon maintenance immunosuppression, is primarily responsible for the morbidity and mortality associated with transplantation. If certain individuals are found to be at low risk for organ rejection, they may forego these measures and thereby avoid the associated hazards. While the methods of the invention are not limited to those carried out with reagents that act by any particular mechanism, our work has led us to believe that the balance between expression of immune or inflammatory genes and anti-apoptotic genes can predict, and perhaps dictates, clinical outcome.

In addition to our discovery that "zero hour" gene expression is predictive of graft function, we found that clinical parameters (which we may also refer to as clinical variables) available at the time of transplantation are also indicative of graft function. These clinical parameters can be determined and considered alone, or in combination with gene expression data, to evaluate a patient's risk for graft failure. Clinical parameters that can be considered include donor status (i.e., was the donor living or deceased at the time the organ or tissue was harvested), donor age, recipient race, degree of HLA matching between donor and recipient patient, and the number of transplants the recipient patient has had previously. In one example, delayed graft function or transplant rejection is predicted by determining donor status (i.e., living vs. cadaver) and the length of warm and cold ischemic times. Where the donor is a cadaver and cold ischemic times are increased (e.g., greater than 10, 15, 20, 25, or 30 hours of cold ischemic time, wherein risk increases with increased ischemic time) the transplant recipient has an increased risk of delayed graft function. In a second example, risk for transplant rejection (e.g., acute rejection) is assessed by determining donor status, warm ischemic time, and the occurrence of delayed graft function. A patient is at the greatest risk of rejecting a transplant (i.e., of acute rejection) when the donor was deceased, the warm ischemic time is increased, and delayed graft function occurs. DGF, as applied to kidney transplantation, generally refers to the need for dialysis in the first week post transplant. DGF can also be considered as a continuous variable such as time to achieving creatinine clearance. In a third example, one can assess the patient's risk of poor graft function six months after transplantation by determining donor status, donor age, recipient race, and the degree of HLA matching. A patient is at the greatest risk of rejecting a transplant (i.e., of acute rejection) when the donor was deceased, the donor was older (e.g., older than 30, 35, 37, 40, 45, 47, 50 years of age, wherein risk increases as donor age increases), the recipient is an African American, and the donor and recipient are HLA mismatched. One or more of the clinical parameters described here can be assessed in connection with any of the methods described above for assessing gene and/or protein expression or activity. Where one or more clinical parameters and one or more gene expression patterns indicate that the patient is at risk for DGF or AR, one can have greater confidence that the patient's prognosis is poor (than one would have had assessing either clinical parameters or gene expression patterns alone).

In addition to the methods described above, the invention features kits that can be used to assess the expression or activity of nucleic acids (e.g., mRNAs) or proteins that play a role in the processes that support successful engraftment (e.g. cytoprotective or anti-apoptotic processes) or that discourage engraftment (e.g., inflammatory or immune processes). The kit can include probes, primers, antibodies or other specific agents that specifically bind to a gene or type of gene described herein or to a protein encoded by that gene (or to a number of different genes and/or proteins). Additional reagents (e.g., buffers, other solutions, secondary antibodies, agents useful in carrying out PCR) and substrates (e.g., membranes, test tubes, glass slides, or other supports in which a reaction can be carried out or upon which the products can be visualized) can also be included. The kits of the invention can also include substances useful in assaying "control" samples and instructions for performing the assay (e.g., instructions printed on a card or pamphlet or given by an audio or visual recording).

Probes (e.g., oligonucleotides) capable of binding the genes described herein (i.e., the genes useful in assessing patient risk) or a subset thereof (e.g., genes that encode proteins associated with inflammation) can be arrayed on a substrate (such as glass or plastic) and such arrays are within the scope of the present invention.

While preferred methods and materials are described below, methods and materials similar or equivalent to those described herein can be used in the practice or testing of the present invention. Wherever allowed by law, the patents, patent applications (including U.S. Ser. No. 60/447,540), and references (including references to public sequence database entries) cited herein are incorporated by reference in their entireties for all purposes. Other features, objects, and advantages of the invention will be apparent from the detailed description, the drawings, and the claims.

BRIEF DESCRIPTION OF THE DRAWINGS

FIG. 1. is a table depicting the results of simple logistic regression, multiple logistic regression and the area under the receiver-operator characteristic curve (ROC AUC) for each of DGF, AR, and 6-month graft function outcomes. Direction represents the direction of each variable that shows its correlation with outcome. P value and $R^2$ value for each variable are given. "Up"=heightened expression; "Down"=decreased expression; "CAD"=cadaver donor type; "AA"=African American. "CIT"=cold ischemic time. "WIT"=warm ischemic time.

FIGS. 5A-5I are lists of genes that can be assessed (alone or in combination with other genes and, optionally, in combination with one or more clinical variables) using the methods and kits of the present invention.

DETAILED DESCRIPTION

Figures 2A, 2B, 2C:
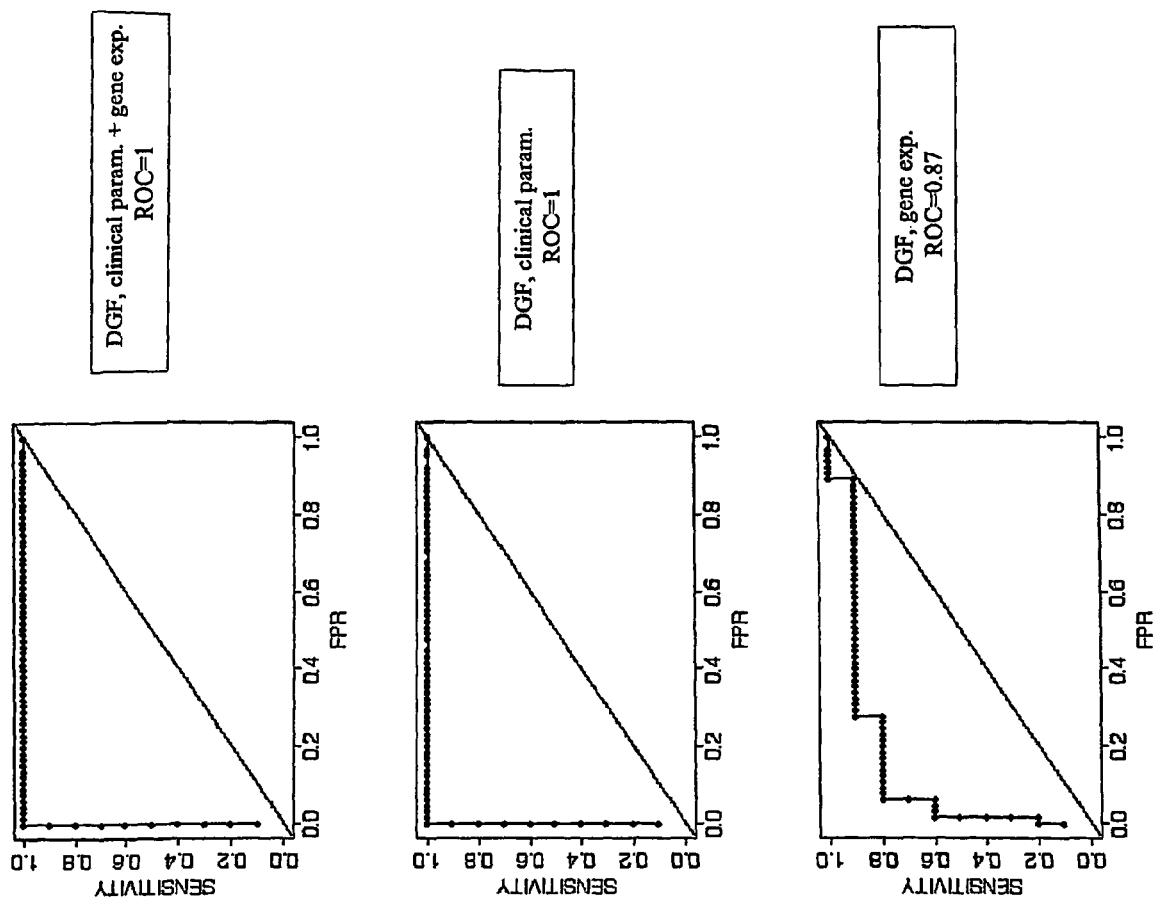
FIGS. 2A, 3A, and 4A are graphs depicting Receiver Operating Characteristic (ROC)-curves for artificial neural nets (ANNs) for DGF, AR and 6-month function, respectively, using clinical and gene variables deemed significant by simple logistic regression. ROC-curves graph the false-positive ratio on the x-axis and the true-positive ratio on the y-axis. ROC AUC=receiver operator characteristic area under the curve, FPR=false positive rate=1−specificity. The diagonal line on each graph depicts the ROC-AUC curve for outcomes due to chance alone.
FIGS. 2B, 3B, and 4B are graphs depicting ROC-curves for ANNs for DGF, AR and 6-month function, respectively, using only clinical variables deemed significant by simple logistic regression.
FIGS. 2C, 3C, and 4C are graphs depicting ROC-curves for ANNs for DGF, AR and 6-month function, respectively, using only gene expression variables deemed significant by simple logistic regression.

The inventions described herein include, but are not limited to, prognostic methods useful in assessing patients who have received a transplant and reagents, optionally packaged as kits, that can be used to carry out those methods (the reagents or kits may have other uses as well). The inventions are based, in part, on our analysis of gene expression in renal allografts and clinical parameters, such as the age of the donor. While other parameters (or case-specific variables) and relevant genes are described further below, we note here that the clinical parameters include one or more variables associated with the recipient (e.g., the recipient's age and/or race); one or more variables associated with the graft (e.g., whether the graft is obtained from a living donor or a cadaver and the ischemic time); and variables associated with the donor (e.g., the donor's age and/or race). The genes that can be assessed include those encoding agents that mediate inflammation, immune activation, and cell death (we may refer to these genes below as "inflammatory," "immune" or "cytoprotective"). Surprisingly, we found that the levels of gene expression could predict the occurrence of DGF, AR, and the quality of later graft function even when analyzed shortly after the transplant was performed (e.g., shortly after vascular anastomosis and tissue reperfusion). We also found that clinical parameters available at the time of transplantation correlate with decreased graft health and can be considered in combination with gene expression to evaluate a patient's risk for an adverse outcome.

In specific embodiments, the invention features methods of assessing a transplant patient's risk of DGF. These methods can be carried out by obtaining (or "providing") a sample of the transplant (e.g., a sample obtained shortly after (e.g., within about 15 minutes of) vascular reperfusion) or a fluid in connection therewith and assessing (a) the expression of one or more of the genes within the sample that encode a member of the tumor necrosis factor family (e.g., TNFα), CD25, a member of the transforming growth factor family (e.g. TGF-β, an interleukin such as IL-6, an adhesion molecule such as ICAM-1, HO-1 (hemeoxygenase-1), and CD3; (b) the ischemic time and, optionally, (c) the source of the transplanted material. The greater the expression of one or more of the listed genes (relative to a control or reference standard) and the longer the period of ischemia, the more likely it is that the patient will experience delayed graft function. Where transplanted material from a cadaver donor is used, the patient's risk is likely to be greater still. In the method just described, as well as any other method of the invention, the genes analyzed may be those expressed by a cell within the transplanted material per se (e.g., by a renal cell, epithelial cell, or myocyte) or within a cell that has invaded the transplanted material (e.g., within a macrophage or other cell associated with the immune response). We may refer to biological samples obtained from the transplanted material per se as "intra-graft" samples.

The invention also features methods of assessing a transplant patient's risk of AR (e.g., rejection within about the first three months (e.g., about two, three, or four months) following transplantation). These methods can be carried out by obtaining (or "providing") a sample of the transplant (e.g., a sample obtained shortly after (e.g. within about 15 minutes of) vascular reperfusion) or a fluid in connection therewith and assessing (a) the expression of one or more of the genes within the sample that encode a member of the tumor necrosis factor family (e.g., TNFα), CD25, a member of the transforming growth factor family (e.g., TGF-β), an interleukin (e.g. IL-6), an adhesion molecule (e.g., ICAM-1), HO-1 and CD3, (b) the ischemic time; (c) the occurrence of DGF and, optionally, (d) the source of the transplanted material. The greater the expression of one or more of the listed genes (relative to a control or reference standard), the longer the period of ischemia, and the greater the delay in graft function, the more likely it is that the patient will experience acute rejection. Where transplanted material from a cadaver donor is used, the patient's risk is likely to be greater still.

The invention also features methods of predicting whether a transplant patient will experience adequate or inadequate (or "poor") graft function after an extended period of time (e.g., 1-2, 2-3, 3-6, or 6-12 months or more) following the transplant procedure. These methods can be carried out by obtaining (or "providing") a sample of the transplant (e.g., a sample obtained shortly after (e.g., within about 15 minutes of) vascular reperfusion) or a fluid in connection therewith and assessing (a) the expression of one or more of the genes within the sample that encode CD25 and a cytoprotective gene such as Bcl-XL, (b) the extent of HLA mismatching and, optionally (c) the source of the transplanted material. The greater the expression of CD25, the lower the expression of Bcl-XL (relative to a control or reference standard), and the greater the extent of the HLA mismatch, the poorer the patient's long-term prognosis. Where transplanted material from a cadaver is used, and/or where the donor is elderly or an African-American, the patient's prognosis is likely to be worse still hird, by calculating ROC-AUC for an ANN, five parameters—(1) increased CD25 and decreased Bcl-XL gene transcripts, (2) the race of the transplant recipient (as African American), (3) the use of renal tissue from cadavers, (4) the age of the donor, and (5) HLA mismatching—were closely correlated with poor graft function at six months post-transplantation.

While pathologic analysis was not predictive, histological examination of a sample of the transplanted material may be carried out in connection with any of the methods of the invention.

Patients Amenable to Analysis:

Essentially any recipient of a transplant can benefit from one or more of the evaluative processes described herein. In accordance with common usage, a transplant can include one or more organs (e.g., a kidney transplant or heart-lung transplant), parts of organs (e.g., a skin graft), cells (e.g., a bone marrow transplant or a transplant of islet cells or other endocrine or exocrine cells), or tissues (e.g., skin, or connective tissues such as cartilage, ligaments, or tendons). More specifically, the techniques described herein can be applied to patients receiving grafts of kidney, heart, lung, liver, pancreas or other endocrine glands, bone, bowel (or other portions of the alimentary canal) or a sensory organ such as an eye; to patients receiving tissues or portions of organs (e.g. transplants of skin, muscle, and connective tissue (as may occur, for example, in the context of reconstructive surgery); to patients receiving cells, such as neurons, glia, epithelial cells (e.g., olfactory epithelial cells), adipocytes, bone marrow cells, blood cells, or stem cells; and to patients receiving cells or tissues derived from stem cells or tissue composites.

Any of the cells transplanted, whether within an intact organ or not, may be genetically modified (e.g., they may carry sequences that express a therapeutically beneficial protein or they may not express (or express to a lesser extent) a gene by virtue of containing, for example, antisense oligonucleotides or siRNAs) that they would otherwise express). Although the recipient of the transplant (who may also be referred to herein as the host or patient) is usually different from the donor of the transplant, that is not necessarily so; patients receiving autologous transplants (which may have been manipulated (e.g., irradiated, drug-treated, or genetically modified) ex vivo) may also benefit from the procedures described here. Patients who receive allografts (which are made between two genetically different individuals of the same species) as well as patients who receive xenografts (which are made between individuals of different species) are amenable to the procedures described here. For example, a human patient receiving transplanted material from a non-human donor (e.g., a pig; porcine neurons, valves, such as heart valves, and other organs or tissues). While we expect the patient or host will most likely be a human, the invention is not so limited; the methods of the invention can be used to assess risk in any animal (e.g., a domesticated pet) that receives a transplant.

As implied by the reference to cadaver donors above, the methods of the invention can be carried out on patients who have received transplanted material from a donor who is deceased. For example, the sample tested can be any RNA-containing tissue (or cells thereof) or fluid (the fluid having RNA by virtue of containing some cells or cellular material). Moreover, the sample can be obtained by methods presently used to obtain a biopsy sample or a fluid sample. As noted above, when the sample includes a biological fluid, the fluid can be one that is "in communication with" the transplanted organ or tissue (i.e., a biological fluid that changes in some reasonably consistent and detectable way in a patient who has received a transplant). For example, urine is in communication with a transplanted kidney or other tissue implanted in or around the kidney or other part of the urinary system when the composition of the urine (or of cells or cellular debris therein) changes in response to the transplanted tissue. Similarly, cerebrospinal fluid (CSF) is in communication with cells transplanted in or around the central nervous system when the composition of the CSF (or of cells or cellular debris therein) changes in response to the transplanted tissue. Whole blood or a fraction thereof (e.g., plasma, serum, or a blood sample containing a particular cell type, such as peripheral blood mononuclear cells (PBMCs)) is also useful. In addition, the methods of the invention can be carried out using bile, bronchoalveolar lavage fluid, pericardial fluid, gastrointestinal fluids, lymph, fluids gathered from an area near or around the graft, or any other fluid that is secreted or excreted by a normally or abnormally functioning graft or that is in communication with the graft.

Fluid samples can be obtained from the patient according to standard methods and tissue-based samples can be obtained by any of the techniques used to obtain biopsy tissue (e.g., by aspiration biopsies, brush biopsies, chorionic villus biopsies, endoscopic biopsies, excision biopsies, needle biopsies (specimens obtained by removal by aspiration through an appropriate needle or trocar that pierces the skin or the external surface of an organ and enters the underlying tissue to be examined)), open biopsies, punch biopsies (trephine), shave biopsies; sponge biopsies, and wedge biopsies. In one embodiment, a fine needle aspiration biopsy is used. In another embodiment, a minicore needle biopsy is used. A conventional percutaneous core needle biopsy can also be used. While it is expected that the sample will be one that is relatively easy to obtain (e.g., a small piece of the transplant or a blood sample), the methods are not so limited.

The methods of the invention, whether aimed at assessing the risk of DGF or AR or the probability of long-term engraftment, can be carried out by assessing gene expression in a sample obtained from the transplant per se (as described above), from RNA-containing fluid in communication with the transplant (also as described above), or both. For example, one can assess the risk of DGF or AR or the probability of long-term engraftment by assessing one or more of the genes and/or clinical parameters described herein within a sample of the grafted material at the time the patient receives the transplant (e.g., about 15 minutes following vascular reperfusion); by assessing those genes and/or clinical parameters in a sample of a biological fluid in communication with the transplanted material at the time the patient receives the transplant; by assessing those genes and/or clinical parameters in such a biological fluid obtained at a subsequent time (e.g., about 1, 2, 3, 4, 5, or 6 or more days following the transplantation procedure); or by assessing any or all of these samples. In fact, fluid samples can readily be obtained and assessed at numerous times (e.g., approximately daily, weekly, or monthly) following the transplantation procedure.

Genes that can be Assessed:

The genes that can be assessed in the methods described herein include, but are not limited to, pro-inflammatory genes (these genes encode proteins associated with inflammatory responses, such as TNFα or TGFβ or genes induced by these growth factors (see FIG. 1), genes encoding cytokines (e.g., Th1 cytokines, which include TNFα and, e.g., IFNγ and lymphotoxin; Th2 cytokines, which include interleukin-4 IL-4) and IL-10; and other interleukins such as IL-6 and IL-2), genes associated with activated T cells (e.g., CD3, CD25), genes encoding adhesion molecules (e.g., ICAM or NCAM), genes encoding co-stimulatory molecules (e.g., B7-1, B7-2, or CD40), genes encoding anti-apoptotic molecules (e.g., A20 or Bcl-$X_L$), genes encoding stress-response proteins (e.g., heme oxygenase-1 (HO-1)), or a combination thereof For example, one can assess CD3, CD25, and TGFβ or CD3, CD25, and TNFα. TGFβ, CD40, and TNFα, or a combination thereof, can be used to predict acute rejection within three months after transplantation when the graft is from a cadaver donor, whereas CD25 and CD3 can be assessed when the graft is from a living donor. More specifically, elevated TNFα expression is associated with DGF and AR, elevated CD3 and CD25 expression are associated with AR within 3 months post-transplantation, and elevated CD25 expression predicts compromised graft function 6 months post-transplantation. More generally, the methods of the invention can employ one or more of the genes described in the Tables and Figures provided herein. Combinations of genes for which expression correlates with an adverse clinical outcome are described in further detail in the examples.

Other genes that can be assessed are provided in FIGS. 5A-5I. These genes can be assessed alone or in combination with one or more additional genes. These genes were identified by screening gene chips with material obtained from living and cadaverous tissue (see the Examples, below).

Clinical Parameters:

Clinical parameters that can be evaluated in assessing patient risk include donor age, recipient age, donor race, number of prior transplants, type of induction therapy (e.g., therapy administered donor or recipient prior to transplant), the length of time the graft was exposed to temperatures other than cold storage temperatures (e.g., temperatures above 4° C.) prior to reperfusion (warm ischemic time), and the length of time the graft in cold storage prior to reperfusion (cold ischemic time). These factors can be considered at the time of transplantation. The fact that we have correlated specific factors such as these with clinical outcomes is particularly useful in monitoring patients at critical stages post-transplantation. Any or any combination of clinical parameters can be assessed alone or in conjunction with an assessment of gene expression (as described above and herein).

The Methods for Assessing Risk:

The sample can be obtained as soon as possible after vascular reperfusion has begun. Preferably, the sample is collected within about fifteen minutes of vascular reperfusion (e.g., 2, 5, 10, 12, 14, 16, 18, 20, or 25 minutes after reperfusion) and up to any time before the surgical incision made to prepare the patient for the transplant is closed. As noted above, the sample can also be obtained subsequent to the transplantation surgery.

The level of gene expression can be determined by assessing the amount of one or more mRNAs or the amount of one or more proteins in the test sample. Methods of measuring mRNA in samples, including any of those described above (which can contain cells from any transplanted organ or tissue) are known in the art. To measure mRNA levels, the cells in the samples can be lysed and the levels of mRNA in the lysates or in RNA purified or semi-purified from the lysates can be determined by any of a variety of methods familiar to those in the art. Such methods include, without limitation, hybridization assays using detectably labeled DNA or RNA probes and quantitative or semi-quantitative RT-PCR methodologies using appropriate oligonucleotide primers. Alternatively, quantitative or semi-quantitative in situ hybridization assays can be carried out using, for example, tissue sections or unlysed cell suspensions, and detectably labeled (e.g., fluorescent or enzyme-labeled) DNA or RNA probes. Additional methods for quantifying mRNA include the RNA protection assay (RPA), cDNA and oligonucleotide microarrays, representation difference analysis (RDA), differential display, EST sequence analysis, and SAGE.

Methods of measuring protein levels in test cells or body fluids are also known in the art. Many of these methods employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin, and detectably labeled avidin or streptavidin (polypeptides that bind to biotin) can be used to detect the presence of the biotinylated antibody. Combinations of these approaches (including "multi-layer sandwich" assays), which are also familiar to those of ordinary skill in the art, can be used to enhance the sensitivity of the methodologies. Some of these protein-measuring assays (e.g., ELISA or Western blot) can be applied to bodily fluids or to lysates of test cells, while others (e.g., immunohistological methods or fluorescence flow cytometry) are better suited for application to histological sections or unlysed cell suspensions. Methods of measuring the amount of label will be depend on the nature of the label and are known in the art. Appropriate labels include, without limitation, radionuclides (e.g., $^{125}I$, $^{131}I$, $^{35}S$, $^{3}H$, or $^{32}P$), enzymes (e.g., alkaline phosphatase, horseradish peroxidase, luciferase, or β-galactosidase), fluorescent moieties or proteins (e.g., fluorescein, rhodamine, phycoerythrin, a GFP, or a BFP), or luminescent moieties (e.g., Qdot™ nanoparticles supplied by the Quantum Dot Corporation, Palo Alto, Calif.). Other applicable assays include quantitative immunoprecipitation or complement fixation assays.

The level of gene or protein expression in the sample obtained from the transplanted tissue can be compared with the level(s) observed in a control sample. Those of ordinary skill in the art are well able to-design appropriate controls. For example, the control sample may be a non-transplanted tissue (e.g., if the donor tissue is a kidney, lung or liver, the control sample can be non-transplanted kidney, lung or liver, respectively).

It may also be useful to compare the level of gene or protein expression to the level of expression of certain constitutively active genes, such as glyceraldehydrate-3-phosphate dehydrogenase (GAPDH), cyclophilin B, or actin. Other such genes (sometimes referred to as "housekeeping" genes) are known in the art.

The information obtained can be used to predict a number of events. For example, it can be used to predict whether the patient will experience delayed graft function or acute rejection (e.g., rejection within weeks (e.g., 1, 2, or 3 weeks) or months (e.g., 1, 2, 3, 4, 5, or 6 months)) from the time of transplantation. The methods can also predict longer-term clinical status (e.g., clinical status more than six months (e.g., 7, 8, 9, 10, or 11 months after transplantation) or more than a year later) and tissue-specific conditions, such as nephropathies.

An elevation in the level of expression of one or more anti-apoptotic genes indicates that the host is likely to retain good (or acceptable) graft function after transplantation (e.g., six months or more following transplantation). Elevated levels of co-stimulatory molecules, on the other hand, indicates that the host is likely to experience poor graft function.

Kits for Assessing Patient Risk:

The invention features kits for assessing a patient's risk for complications following organ transplantation. The kits can include reagents for evaluating the expression or activity of nucleic acids (e.g., mRNAs) or proteins that play a role in the processes that support successful engraftment (e.g., cytoprotective or anti-apoptotic processes) or that discourage engraftment (e.g., inflammatory or immune processes). Kits for evaluating expression of nucleic acids can include, for example, probes or primers that specifically bind a nucleic acid of interest (e.g., a nucleic acid, the expression of which correlates with increased risk of complications from transplant surgery). The kits for evaluating nucleic acid expression can provide substances useful as a "control" or standard (e.g., a sample containing a known quantity of a nucleic acid to which test results can be compared, and/or with which one can assess factors that may alter the readout of a diagnostic test, such as variations in an enzyme activity or binding conditions). Kits for assessing nucleic acid expression can further include other reagents useful in assessing levels of expression of a nucleic acid (e.g., buffers, and other reagents for performing PCR reactions, or for detecting binding of a probe to a nucleic acid). In addition to, or as an alternative, kits can include reagents for detecting proteins (e.g., antibodies). The kits can provide instructions for performing the assay used to evaluate gene expression (e.g., instructions printed on a card or pamphlet or given by an audio or visual recording) and/or instructions for determining risk based on the results of the assay. For example, the instructions can indicate that levels of expression of a gene of interest (e.g., relative to a standard or a control), correlate with increased risk for an adverse outcome from transplantation. Kits can also provide instructions, containers, and other reagents for obtaining and processing samples for analysis.

Exemplary kits for assessing patient risk include reagents for evaluating expression levels of a gene or genes associated with inflammation such as a tumor necrosis family members (e.g., TNFα), genes associated with lymphocyte activation (e.g., CD3, or CD25), transforming growth factor family proteins (e.g. TGF-β), an interleukin (e.g., IL-6), adhesion molecules (e.g., ICAM-1), stress-response proteins (e.g., HO-1), or cytoprotective proteins (e.g., Bcl-$X_L$) in a sample obtained from a graft. Kits for determining specific outcomes can assess expression of gene(s) reported herein to be correlated with the outcome. For example, reagents for detection of CD25 and/or Bcl-$X_L$ expression can be provided in a kit that is used for determining risk for poor graft function in the months following transplantation. Other useful reagents will also be apparent from our findings.

Optionally, any part of the kit that may be opened within an operating theater can be sterilized prior to sale or at its destination.

Methods for Developing Personalized Treatment Plans:

Information gained by way of the methods described above can be used to develop a personalized treatment plan for a transplant recipient. Accordingly, the invention further provides methods for developing personalized treatment plans for transplant recipients. The methods can be carried out by, for example, carrying out any of the methods of gene analysis described above and, in consideration of the results obtained, designing a treatment plan for the patient whose transplant is assessed. If the levels of gene expression indicate that the patient is at risk for an undesirable clinical outcome (e.g., developing DGF, AR, or compromised graft function at, for example, 6 months post-transplantation), the patient is a candidate for treatment with an effective amount of an anti-rejection agent. Depending on the level of gene expression the patient may require a treatment regime that is more aggressive than a standard regime, or it may be determined that the patient is best suited for a standard regime. When so treated, one can treat or prevent transplant rejection (or, at least, prolong the time the transplanted organ functions adequately). Conversely, a different result (i.e., a different level of expression of certain genes) may indicate that the patient is not likely to experience an undesirable clinical outcome. In that event, the patient may avoid anti-rejection agents and their associated side effects.

The anti-rejection therapy, if deemed advisable, can be carried out with any of the presently used therapeutic agents (e.g., immunosuppressive agents). Generally, these agents are suspended in pharmaceutically-acceptable carriers (e.g., physiological saline) and administered orally or by inhalation or intravenous infusion, or injected or implanted in a variety of ways (e.g., subcutaneously or intramuscularly). The standard dosage may be increased or decreased, depending on the results of the gene expression analysis. For example, dosage may be at least 2-fold, 3-fold, 4-fold, 6-fold, 8-fold, 10-fold, 20-fold, 50-fold, 100-fold, or 150-fold more or less than the dosage the patient would ordinarily receive.

The following examples are meant to illustrate, not limit, the invention.

EXAMPLES

We have tested the hypothesis that analyzing transplanted tissue (here, renal allografts) for expression of genes that encode pro-inflammatory molecules, adhesion molecules, molecules that mediate immune activation, and anti-apoptotic proteins approximately 15 minutes after vascular reperfusion (a time frame that falls within the "zero-hour") can be used to predict the occurrence of delayed graft function (DGF), acute rejection (AR), and the quality of graft function six months or more after transplantation.

We obtained intra-operative kidney biopsies from 75 renal allografts 15 minutes after completion of the vascular reperfusion process and analyzed them by routine pathological methods and real-time polymerase chain reaction (PCR). The PCR was designed to detect transcription of certain pro-inflammatory cytokines, T cell markers, and anti-apoptotic or cytoprotective genes. Clinical variables and outcomes were also analyzed.

The studies we carried out are presented in detail below. In summary, our results demonstrate that, first, by calculating the area under the curve of receiver operator characteristic curve (ROC-AUC) for an artificial neural net (ANN), three parameters—(1) the abundance of TNF-α, CD25, TGF-β, A20, IL-10 and ICAM-1 gene transcripts detected in the samples obtained at the "zero-hour," (2) the use of renal tissue from cadavers and (3) an increased ischemic time—were closely correlated with the occurrence of DGF. Second, by calculating ROC-AUC for an ANN, four parameters—(1) the abundance of TNF-α, CD25, TGF-β, IL-6, ICAM-1, HO-1, and CD3 gene transcripts (in samples obtained at the "zero-hour"), (2) the use of renal tissue from cadavers, (3) an increased warm ischemic time, and (4) DGF—were correlated with AR during the first 3 months. Third, by calculating ROC-AUC for an ANN, five parameters—(1) increased CD25 and decreased Bcl-$X_L$ gene transcripts, (2) the race of the transplant recipient (as African American), (3) the use of renal tissue from cadavers, (4) the age of the donor, and (5) HLA mismatching—were closely correlated with poor graft function at 6 months post-transplantation. Pathologic analysis was not predictive. Intragraft gene expression profiling at the "zero-hour" allowed us to make highly accurate predictions for not only early AR, but also for the quality of the graft immediately and up to at least six months post-transplantation. Analysis of the molecular status of the allograft at the time of reperfusion enables refined, individualized treatment of graft recipients, and it also helps elucidate basic mechanisms of allograft dysfunction.

Our studies were conducted with tissue obtained from 75 renal allografts. Thirty-one of the grafts were obtained from cadavers and 44 were obtained from living patients. The transplants were performed at Beth Israel Deaconess Medical Center (Boston, Mass., USA) between September of 1999 and June of 2002. Patients were excluded from the study if they had a bleeding diathesis or required anti-coagulant therapy. Subsequent to collection, three of the samples were discarded due to RNA degradation.

The intra-operative immunosuppressive regimen consisted of 1.5 mg/kg of thymoglobulin (Sangstat, Fremont, Calif.) or 20 mg of anti-CD25 antibody (Simulect®; Novartis, East Hanover, N.J.) and Solumedrol (500 mg, administered intravenously). Maintenance immunosuppressive regimens included administration of calcineurin inhibitors (tacrolimus (Fujisawa, Deerfield, Ill.) or cyclosporin (Novartis, East Hanover, N.J.), prednisoline, and mycophenolate mofetil (CellCept; Roche, Nutley, N.J.)). Five patients received sirolimus (Wyeth-Ayerst, St. Davids, Pa.), prednisolone, and mycophenolate mofetil.

To obtain the samples, an intra-operative wedge biopsy of the allograft was performed fifteen minutes after reperfusion. Biopsy specimens were immediately split into two portions. One portion was processed for histopathology, and the other portion was directly snap-frozen in liquid nitrogen and was stored at −80° C. prior to RNA isolation.

Total RNA was isolated from homogenized tissue samples using a commercially available kit (Rneasy®, Qiagen Inc., Chatworth, Calif.; Avihingsanon et al., *Transplantation* 73:1079-1085, 2002). Reverse transcription of 1 µg of RNA was performed using Multiscribed Reverse Transcriptase Enzyme (PE Applied Biosystems, CA).

Real-time PCR was performed using the ABI 7700 sequence detector system (Applied Biosystems, Foster City, Calif.). PCR amplification was performed in a total volume of 25 µl containing 5 µl of cDNA sample, 0.6 µM of forward and reverse primer, 0.2 µM of TaqMan® probe and 12.5 µL of TaqMan® Universal PCR mastermix (Applied Biosystems, Foster City, Calif.). Amplification was performed using primer and hybridization probe sets of the following targeted mRNAs (see Table 1): tumor necrosis factor-alpha (TNFα), transforming growth factor-beta (TGFβ), gamma interferon (IFNγ), interleukin 10 (IL-10), CD3-ε, CD25, CD40, intercellular adhesion molecule 1 (ICAM-1), platelet endothelial cellular adhesion molecule (PECAM), A20, Bcl-$X_L$, Bcl-2, and 18s ribosomal RNA as a house-keeping gene.

TABLE 1

| Gene | Genbank Acc'n. No. | Primer/probe sequences |
|---|---|---|
| | | Proinflammatory genes |
| TNF-α | NM_000594 | PE Appliedbiosystems [Meaning? Commercial source?] |
| TGF-β | XM008912 | Sense 5'-ccc tgc ccc tac att tgg ag-3' (SEQ ID NO: 1) |
| | | Antisense 5'-ccg ggt tat gct ggt tgt aca-3' (SEQ ID NO: 2) |
| | | Probe 5'FAM cacgca gta cag caa ggt cct ggc c TAMRA3' |
| | | (SEQ ID NO: 3) |
| IL-6 | | PE Appliedbiosystems |
| | | Th1/Th2 cytokines |
| IFN-γ | XN006883 | Sense 5'-cag atg tag cgg ata atg gaa ctc tt-3' (SEQ ID NO: 4) |
| | | Antisense 5'-gag aca att tgg ctc tgc att att tt-3' |
| | | (SEQ ID NO: 5) |
| | | Probe 5'FAM tca ctc tcc tct ttc caa ttc ttc aaa atg cct aa- |
| | | TAMRA3' (SEQ ID NO: 6) |
| IL-10 | | PE Appliedbiosystems |
| | | Activated T-cell markers |
| CD3-ε | NM_000733 | Sense 5'-aag aaa tgg gtg gta tta cac aga ca-3' (SEQ ID NO: 7) |
| | | Antisense 5'-tgc cat agt att tca gat cca gga t-3' |
| | | (SEQ ID NO: 8) |
| | | Probe 5'FAM cca tct ctg gaa cca cag taa tat tga cat gcc |
| | | TAMRA3' (SEQ ID NO: 9) |
| CD25 | NM_000417 | PE Appliedbiosystems |

TABLE 1-continued

List of genes analyzed.

| Gene | Genbank Acc'n. No. | Primer/probe sequences |
|---|---|---|
| | | Co-stimulatory molecules |
| CD40 | NM_001250 | PE Appliedbiosystems |
| | | Adhesion molecules |
| PECAM | | Sense 5'-cct cag aat cta cca aga gtg aac tg -3' (SEQ ID NO: 10)<br>Antisense 5'-act taa tgt gga gct gag ctc ctt-3' (SEQ ID NO: 11)<br>Probe 5'FAM cac cgt gac gga atc ctt ctc tac ac TAMRA3' (SEQ ID NO: 12) |
| ICAM-1 | NM_000201 | Sense 5'-cgg ctg acg tgt gca gta ata c-3' (SEQ ID NO: 13)<br>Antisense 5'-ctt ctg aga cct ctg gct tcg t-3' (SEQ ID NO: 14)<br>Probe 5'FAM tct aca gct ttc cgg cgc cca a TAMRA3' (SEQ ID NO: 15) |
| | | Anti-apoptotic genes |
| HO-1 | | |
| A20 | M59465 | Sense 5'-ctg ccc agg aat gct aca gat ac-3' (SEQ ID NO: 16)<br>Antisense 5'-tta aca agt gga aca gct cgg att-3' (SEQ ID NO: 17)<br>Probe 5'FAM cca ttg ttc tcg gct atg aca gcc atc TAMRA3' (SEQ ID NO: 18) |
| Bcl-X$_L$ | Z23115 | Biosource, Camarillo, CA |
| Bcl-2 | | PE Appliedbiosystems |
| | | House-keeping gene |
| 18s ribosomal RNA | X03205 | PE Appliedbiosystems |

To quantify the levels of mRNA, expression of the target genes was normalized against that of the housekeeping gene, 18s ribosomal RNA. The levels of targeted mRNA were expressed as a relative fold difference between cDNA of the biopsies and a calibrated sample (User bulletin #2, ABI Prism® 7700 sequence detection system; The Perkin Elmer Corporation, 1997).

The clinical variables we assessed included the recipient's age and race, whether the recipient had previously received a transplant (and, if so, how many), the type of induction therapy, ischemic time (warm ischemic time (WIT) in the event the donor was a living donor and cold ischemic time (CIT) in the event the donor was a cadaveric donor), donor HLA type, donor age, and donor race.

The clinical variables were retrieved from computerized medical records and chart reviews (see Table 2). The transplant outcomes included early graft function, biopsy-proven acute rejection within three months post-transplantation, and serum creatinine levels six months post-transplantation. DGF was defined as a requirement for dialysis during the first week post-transplantation in the absence of vascular complications or urinary tract obstruction. Poor graft function was defined as a serum creatinine level equal to or in excess of 2 mg/dL at six months post-transplantation.

Normalized RNA expression data were scaled to unity to account for variation between experiment runs. First, simple logistic regression was performed for each variable on each of the three clinical outcomes of interest. For each outcome, each variable that demonstrated a P value <0.05 is listed in the table in FIG. 1, along with the variable's $R^2$ value. Multiple logistic regression was then performed to determine combinations of time-zero intragraft genes and clinical variables that correlate with each outcome of interest, using only those genes and clinical variables that demonstrated individual P values <0.05, as described above. For the purposes of training artificial neural nets (ANNs), missing data points were imputed from the 5-nearest neighbors (Troyanskaya et al., *Bioinformatics* 17:520-525, 2001), as measured by Euclidean distance. Of a total of 2700 data points, only 260 (9.6%) were missing. Missing data points were evenly distributed within each outcome (AR vs. no rejection, DGF vs. no DGF, and poor 6-month outcome vs. good 6-month outcome). Gene expression variables selected for multiple logistic regression were then used to train an ANN for each outcome of interest, utilizing the imputed data. Leave-one-out cross validation was performed on each ANN model, and the area under the receiver-operator characteristic curve (ROC AUC) was then calculated to determine the performance of each ANN for each outcome. Logistic regression and nearest neighbor calculations were performed in the R programming environment (www.r-project.org). The ANN was implemented and validated in PERL (www.perl.org).

As noted above, renal allograft biopsies were studied from 75 patients. Of these, ten patients developed DGF; ten patients experienced an episode of AR within 3 months post-transplantation; ten patients had poor graft function at 6 months post-transplantation. Five patients died with a functioning graft during the follow-up period. Two live kidney recipients died, one from cardiovascular disease and one from lymphoproliferative disease. Three cadaver kidney recipients died as a result of sepsis.

Table 2 summarizes the clinical data. Patients who received grafts from cadavers experienced DGF and poor graft function at six months more frequently than did patients who received grafts from living donors. There were no differences in donor or recipient ages and immunosuppressive regimens between patients with DGF and without DGF. Likewise, no differences in these parameters were found between patients who experienced AR and those who did not. Poor graft function at six months post-transplant occurred more frequently in the recipients of kidneys from older donors.

TABLE 2

| | Patient Characteristics | | | | | |
|---|---|---|---|---|---|---|
| | Delayed graft function | | Acute rejection within 3 mo.[#] | | Graft function at 6-mo.[#] | |
| | | | | | Poor | Good |
| | Yes (n = 10) | No (n = 65) | Yes (n = 10) | No (n = 65) | (SCr ≥ 2 mg/dl) (n = 10) | (SCr < 2 mg/dl) (n = 60) |
| Donor characteristics | | | | | | |
| Living donor/Cadaver donor | 1/9 * | 43/22 | 3/7 | 41/24 | 2/8 * | 40/20 |
| Mean donor age (+/−SD) | 35 +/− 12 | 40 +/− 10 | 43 +/− 13 | 39 +/− 10 | 49 +/− 12 * | 38 +/− 10 |
| Cadaveric donor age (+/−SD) | 51 +/− 10 | 51 +/− 10 | 50 +/− 8 | 53 +/− 11 | 56 +/− 8 | 47 +/− 10 |
| Living donor age (+/−SD) | 45 | 46 +/− 11 | 44 +/− 5 | 46 +/− 12 | 42 +/− 4 | 46 +/− 12 |
| Cold ischemia time (+/−SD) | 19 +/− 6 | 15 +/− 3 | 18 +/− 5 | 15 +/− 5 | 15 +/− 3 | 15 +/− 4 |
| Recipient characteristics | | | | | | |
| Mean recipient age (+/−SD) | 50 +/− 9 | 48 +/− 11 | 48 +/− 7 | 48 +/− 11 | 52 +/− 9 | 46 +/− 11 |
| Second transplant | 0 | 3 | 0 | 3 | 1 | 2 |

* $p < 0.05$,
[#] censored for death,
SCr: serum creatinine.

The Correlation Between Zero-Hour Intra-Graft Gene Expression and DGF:

Cadaver donor type, prolonged warm and cold ischemic times and the abundance of TNF-α, CD25, TGF-β, A20, IL-10 and ICAM-1 transcripts detected in "zero-hour" were individually correlated with the occurrence of DGF (FIG. 1). In particular, TNF-a gene expression was highly correlated with DGF ($R^2=0.69$, P-value <0.001). The multiple logistic regression model, which includes these gene expression events and clinical variables, closely correlated with the occurrence of DGF ($R^2=0.98$). A ROC-AUC of 1 indicates faultless discrimination and a ROC-AUC of 0.5 indicates the effects of chance alone. The ROC-AUC values for the ANN for DGF, including all significant variables, the significant clinical variables only, and the significant gene variables only were 1.0, 1.0, and 0.87, respectively. This demonstrates that either clinical variables or gene expression can predict the occurrence of DGF with very high sensitivity and specificity (FIGS. 2A, 2B, and 2C). The incidence of DGF was 14.5% during the study period. Analysis of the eight variables reported here (i.e., abundance of TNF-α, CD25, TGF-β, A20, IL-10 and ICAM-1 transcripts, and cadaver donor type, and prolonged warm and cold ischemic times) therefore reflects an improved ability to identify patients at increased risk for DGF.

"Zero-Hour" Intragraft Gene Expression, Clinical Variables Events and Prediction of Acute Rejection (AR) Episodes.

Figure 3A:
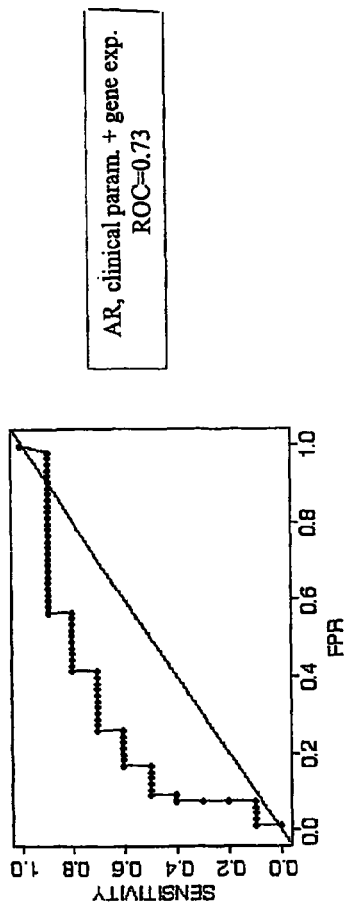
Figure 3B:
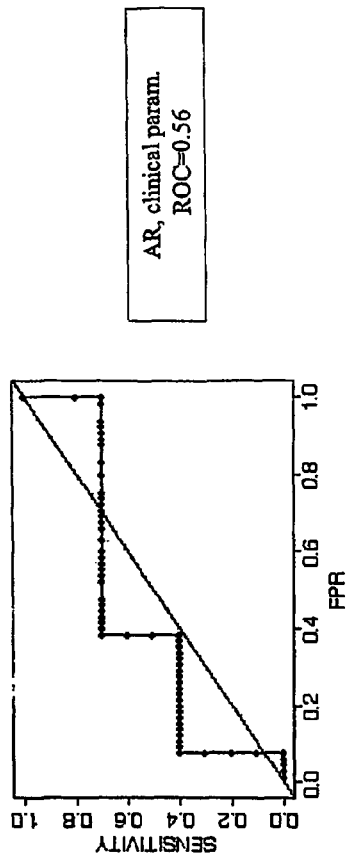
Figure 3C:
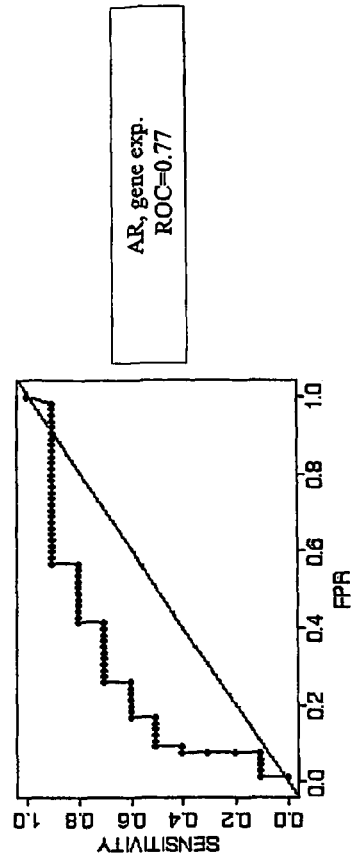

The cadaver donor type, ischemic time, an occurrence of DGF and the abundance of TNF-α, CD25, TGF-β, IL-6, ICAM-1, HO-1, and CD3 transcripts detected in "zero-hour" samples were individually significantly correlated with an episode of AR (FIG. 3C). The multiple logistic model including these gene expression events and clinical variables correlated with AR during the first three months ($R^2=0.887$). The ROC-AUC values for the ANN for AR, including all significant variables, the significant clinical variables only, and the significant gene variables only were 0.73, 0.56, and 0.77, respectively, demonstrating that gene expression values can predict the occurrence of AR with high sensitivity and specificity (FIG. 3C), exceeding the combined and clinical variable models (FIGS. 3B and 3A). The incidence of AR was 12% during the study period. Therefore, analysis of the quantitative expression of a limited panel of gene expression events and clinical variables greatly aids identification of rejection-prone patients.

"Zero-Hour" Intragraft Gene Expression, Clinical Variables, and Prediction of 6-Month Graft Function.

With respect to six-month graft function, African American recipient race (African American), cadaver organ donation, increased donor age, an episode of AR during the first three transplant months, episode of the degree of HLA mismatching, increased CD25 expression, and decreased Bcl-$X_L$ gene expression were individually correlated associated with poor six-month graft function (FIG. 1) (p<0.05).

Since AR during the first 3 months is not a "time-zero" event, multiple logistic regression was performed with and without AR. The multiple logistic model, including all five clinical variables, increased expression of the T cell activation gene CD25, and decreased expression of the cytoprotective Bcl-$X_L$ gene showed that co-expression of CD25 and A20 genes correlated modestly with poor graft function six months post-transplantation ($R^2=0.48$). Removing AR from the multiple logistic regression model did not change the model's performance ($R^2=0.48$). The ROC-AUC values for the ANN for six-month graft function, including all significant variables except AR, the significant clinical variables only (except AR), and the significant gene variables only were 0.84, 0.73, and 0.78, respectively, demonstrating that gene expression values can predict the occurrence of six-month function with high sensitivity and, specificity (FIGS. 4A, 4B, and 4C), exceeding the clinical variable model.

Histologic Analysis of "Zero-Hour" Biopsies and Prediction of Clinical Outcomes.

The histology of "zero-hour" biopsies was evaluated without knowledge of clinical outcomes. At most, minor changes were noted. Rare focal infiltration of monocytes/macrophages was seen in five samples. Two of these five samples were from patients with DGF. Glomerulosclerosis involving less than 10% of glomeruli was found in three samples. One sample was from a patient who ultimately had poor graft function at six months. Zero hour biopsies from patients who developed AR during the first three months post-transplantation failed to reveal abnormalities. The pathologic analysis did not predict DGF or AR or the level of graft function six months post-transplantation.

Additional Remarks

Figures 4A, 4B, 4C:
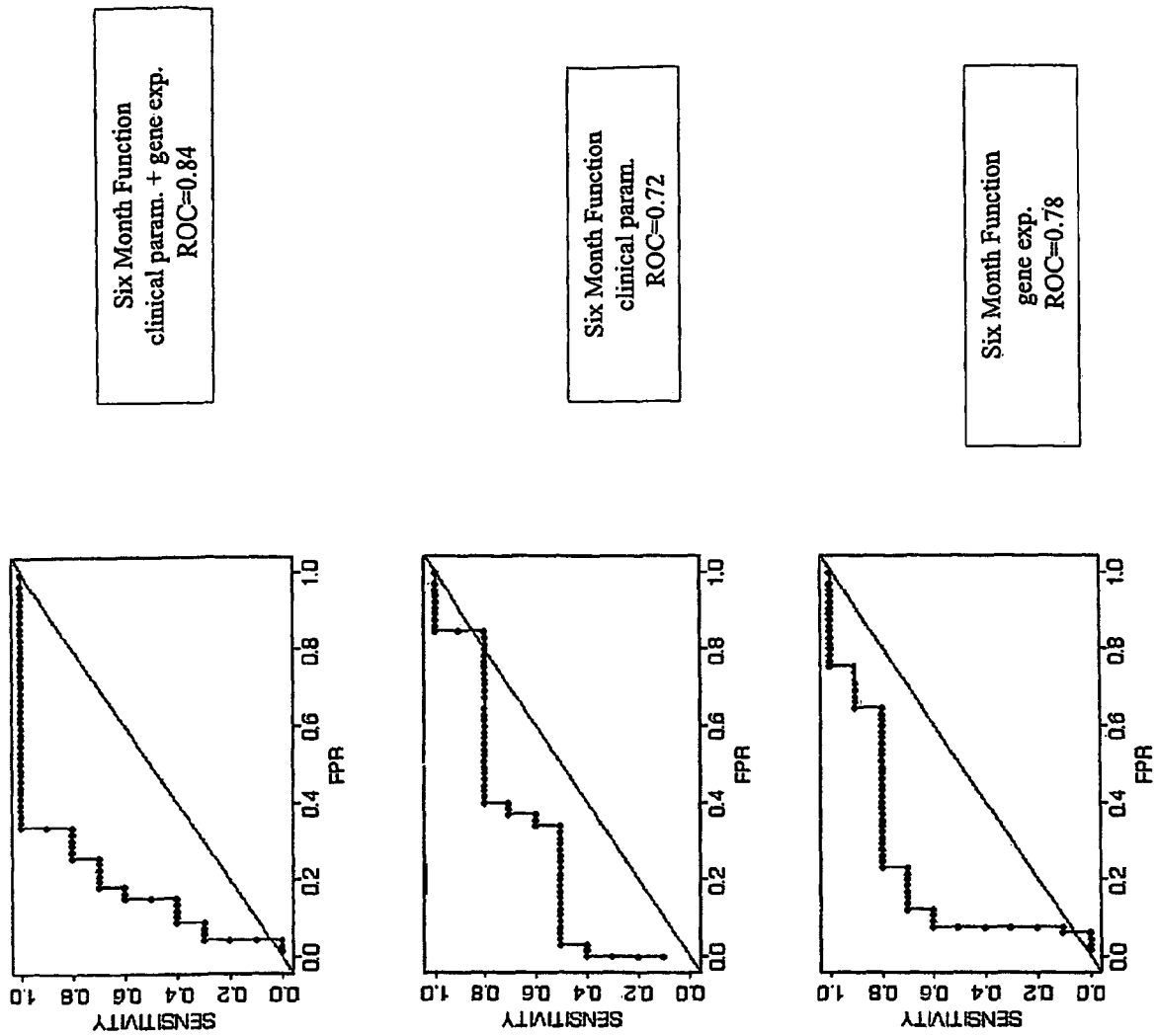

Our work demonstrates that the transcriptional profile (here, a PCR-based transcriptional profile) of a transplanted organ at the "zero-hour," combined with clinical information available at the time of transplant (see FIG. 1), can be used to accurately predict post-transplant clinical outcomes including DGF, early AR, and the quality of renal function at least six months post-transplantation. Standard histopathology at the "zero-hour" is not informative. The relative abundance of pro-inflammatory and adhesion molecule gene transcripts in "zero-hour" biopsies, cadaver-donated grafts, and prolonged warm and cold ischemia times collectively and accurately predicts the occurrence of DGF immediately following transplantation (FIGS. 1, 2A, 2B, and 2C). The abundance of T-cell activation and pro-inflammatory gene transcripts, cadaver donor, prolonged warm ischemic time and the presence of DGF collectively and accurately predict the occurrence of acute rejection within the first 3 months following transplantation (FIGS. 1, 3A, 3B, and 3C). Furthermore, poor graft function at six months post-transplantation is collectively predicted by an African-American recipient, cadaver donated grafts, increased donor age, episode of poor HLA mismatching, increased CD25 and decreased Bcl-$X_L$ gene expression in "zero-hour" biopsies (FIGS. 1, 4A, 4B, and 4C). ANN models evaluating the predictive utility of clinical variables alone and gene expression values alone show that gene expression data are important components of the predictive models, surpassing the combined model for AR, and surpassing the clinical variables for six-month graft function (FIGS. 2, 3, and 4).

DGF predisposes patients to morbidity, susceptibility to the nephrotoxicity of calcineurin inhibitors, poor detection of early AR, and a complex post-operative course (Amend et al. *Handbook of Kidney Transplantation*. 3rd ed. Philadelphia, Pa., Lippincott Williams & Wilkins, 2001). Cadaver donated kidneys, increased ischemic times and the abundance of TNFα, CD25, TGFβ, A20, IL-10 and ICAM-1 transcripts detected in "zero-hour" collectively and accurately predict DGF (FIG. 1), thereby emphasizing the utility of intragraft gene expression as a prognostic tool. We designed our studies, in part, given the realization that donors with the high-producing TNFα genotype are at risk for increased early graft loss (Gandhi et al., *Transplant Proc* 33:827-828, 2001) and, in a study of ischemia/reperfusion injury in rat kidneys, there is a relationship between TNFα, TGFβ, and ICAM-1 expression and the duration of ischemia/reperfusion time (Donnahoo et al., *Am. J. Physiol.* 277:R922-R929, 1999; Dragun et al., *Kidney Int.* 58:2166-2177, 2000; Dragun et al., *Kidney Int.* 54:2113-2122, 1998). In the rat model, blockade of TNFα or ICAM-1 blunted renal injury resulting from ischemia/reperfusion (Donnahoo et al., *Am. J. Physiol.* 277:R922-R929, 1999; Dragun et al. *Kidney Int.* 54:2113-2122, 1998).

It is remarkable that the molecular status of an allograft at the "zero-hour," considered in the context of clinical variables known at the time of transplantation (or that occur early within the post-transplant period), can provide insight into the vulnerability of the graft to AR, particularly given the period of time that elapses between the "zero-hour" biopsy and the development of AR. Heightened intra-graft expression of T cell (CD3), T cell activation (CD25) and pro-inflammatory genes accurately identified AR-prone recipients (FIGS. 1 and 3C), thereby providing a means to test the value of individualized immunosuppressive treatment regimens.

The very early presence of T cell (CD3) transcripts within the biopsy at the "zero-hour" in patients at heightened risk of early rejection suggests that pre-immune anti-donor T cells are present in these individuals or that the rejection-prone allografts attract non-activated T cells more quickly than other renal allografts. As detection of T cell activated related CD25 transcripts was observed only 15 minutes post-reperfusion, it is notable that CD25 transcripts cannot be readily detected within 15 minutes of activation in a population of peripheral blood leukocytes stimulated with potent polyclonal mitogens in vitro (Leonard et al., *Proc. Natl. Acad. Sci. USA* 82:6281-6285, 1985). Perhaps rejection episodes often occur in patients with undetected T cell anti-donor immunity present at the time of transplantation; the methods of the present invention provide a means to discover such immunity.

Ischemia or reperfusion injury can initiate an inflammatory response leading to an increased level of host immunologic reactivity (Lu et al., *Kidney Int.* 55:2157-2168, 1999; Lu et al., *Graft* 2:S36-S43, 1999; Kouwenhoven et al., *Kidney Int.* 69:1142-1148, 2001; Penfield. et al., *Kidney Int.* 56:1759-1769, 1999). Kidney recipients whose allografts bear an abundance of CD3 or CD25 transcripts, particularly those patients whose allografts also bear an abundance of transcript for pro-inflammatory cytokines, TNFα, TGFβ, IL-6 and ICAM-1 at the "zero-hour" warrant meticulous monitoring for rejection. Robust expression of both T cell and pro-inflammatory genes is particularly ominous (FIG. 1). The methods utilized to follow patients at heightened risk for AR might include transcriptional profiling of urinary sediment or peripheral blood cells for molecular markers of acute rejection (Li et al., *N. Engl. J. Med.* 344:947-954, 2001; Vasconcellos et al., *Transplantation* 66:562-566, 1998).

Persistent vascular endothelial cell expression of the cytoprotective genes HO-1 and A20 is noted in long-term surviving cardiac xenografts (Bach et al., *Nature Med.* 3:196-204, 1997; Bach et al., *Immunol. Today* 18:483-486, 1997) whereas these protective genes were expressed in the vascular endothelial cells of rejecting kidney allografts in humans (Avihingsanon et al., *Transplantation* 73:1079-85, 2002). HO-1 expression follows ischemic/reperfusion injury and is believed to limit graft injury (Blydt-Hansen et al., *J. Am. Soc. Nephrol.* 14:745-754, 2003). In this study, heightened "zero-hour" HO-1 gene expression is linked with the later occurrence of AR. Expression of A20, a TNF-inducible gene, is associated with the abundance of TNFα and the occurrence of DGF. Although some aspects of our invention relate more to predictive and diagnostic methods, we note that the expression of stress-responsive genes (e.g., HO-1 and A20) in DGF- or AR-prone zero-hour renal allografts may serve to limit injury in these damaged allografts. Accordingly, modifying grafted tissue to express or overexpress these genes (or these types of genes) or biologically active variants thereof, is another aspect of our invention (see Soares et al., *Immunol. Today* 20:434-437, 1999).

While increased expression of HO-1 and A20 in the "zero-hour" biopsy predicted adverse clinical outcomes, decreased expression of Bcl-$X_L$ was correlated with compromised graft function at six months post-transplantation. Unlike HO-1 and A20 gene activation, ischemia-reperfusion or TNFα are not known to trigger Bcl-$X_L$ expression. Hence, decreased Bcl- $X_L$ expression may render grafts susceptible to injury as embodied by impaired graft function at six months.

Protocols for the Affymetrix Oligonucleotide Microarray System.

As the Affymetrix oligonucleotide arraying technology we used is highly standardized, we only summarize the protocol here.

Step 1: preparing and labeling the cRNA target. Total RNA was isolated using the Qiagen RNAeasy® kit. cDNA synthesis from 5-20 mg total RNA will use reverse transcriptase (Gibco BRL SuperScript Choice kit) and a T7-oligo (dT) primer to generate the first strand, followed by RNAse H nicking and DNA polymerase I to generate the second strand. In vitro transcription with biotinylated UTP and CTP using the Enzo Diagnostics BioAssay High Yield RNA Transcript Labeling kit will generate labeled cRNA; we get a 40- to 80-fold linear amplification from total RNA to labeled cRNA.

Step 2: hybridization and scanning of GeneChips. Forty micrograms of biotinylated RNA was fragmented to lengths of 50 to 150 nucleotides and hybridized overnight onto Affymetrix human U1334A GeneChips containing ~22000 different genes each. Control Test 3 chips were used to ensure that proper handling was used, RNA extraction was performed properly, and probe labeling occurred efficiently. The Affymetrix arrays were washed, stained with streptavidin-phycoerythrin, and then scanned to quantitate the simultaneous expression of the arrayed elements. The scanned files were then uploaded securely for further annotation and analysis.

Analysis: We calculate the fold differences in gene expression associated with various clinical and biological states (e.g., predisposition of a graft to be rejected or have reduced function after transplantation), in an attempt to identify those genes with the greatest and least changes between states. We will use different cut-off thresholds for significance in fold-change depending on the "noise" or sources of variation analyses that we observe. In our experience, the reproducibility of fold differences of 1.5 or less can be poor, and a higher threshold (e.g. three-fold) may still yield many novel genes and profiles to investigate, even if it is more restrictive. The "profile" may prove to be more informative than the actual fold-increase in a given gene. A list of genes displaying changes in expression between living and cadaver tissue are presented in FIGS. 5A-5I. Expression of these genes can be evaluated in assessing patient risk.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a transplant recipient with an increased risk of delayed graft function or an increased risk of graft rejection, the method comprising:
   (a) obtaining an intra-graft sample from a graft transplanted into the recipient, wherein the sample is obtained from the recipient during the operation in which the graft was transplanted and after a point in time when the graft was transplanted and substantially reperfused;
   (b) determining a level of expression of one or more genes selected from the group consisting of TNF-α and CD25 in the sample, wherein an increase in the level of expression in the one or more genes relative to a control sample or a reference standard indicates that the transplant recipient has an increased risk of delayed graft function or an increased risk of graft rejection; and
   (c) administering to the transplant recipient identified as having an increased risk of delayed graft function or an increased risk of graft rejection an immunosuppressant.

2. The method of claim 1, wherein the graft is (a) an organ comprising a kidney, a heart, a lung or a portion or lobe thereof, a liver or a portion thereof, a pancreas or a portion thereof, a bone, bone marrow, or a segment of bowel or other portion of the alimentary canal or (b) a tissue or a collection of cells comprising myocytes, alveolar cells, hepatocytes, islet cells, stem cells, epithelial cells, neurons, or glial cells.

3. The method of claim 1, wherein the sample comprises a fluid that is produced by the graft; that comes into physical contact with the graft; or that otherwise communicates with the graft in such a way that the fluid contains RNA present within the graft or the immune cells that invade the graft.

4. The method of claim 1, wherein, in addition to TNF-α or CD25, the one or more genes comprises a gene that encodes a cytokine, CD3, a gene that encodes an adhesion molecule, or a gene that encodes a co-stimulatory molecule.

5. The method of claim 4, wherein the gene that encodes a cytokine encodes IL-1, IL-2, IL-3, IL-4, IL-5, IL-6, IL-7, IL-8, IL-9, IL-10, IL-11, IL-15, IL-21, or interferon-gamma (IFNγ).

6. The method of claim 4, wherein the gene that encodes an adhesion molecule encodes ICAM-1.

7. The method of claim 4, wherein the gene that encodes a co-stimulatory molecule encodes B7-1, B7-2, or CD40.

8. The method of claim 1, wherein, in addition to TNF-α or CD25, the one or more genes comprises a gene that encodes an anti-apoptotic or cytoprotective protein; wherein a decrease in the level of expression of the gene that encodes an anti-apoptotic or cytoprotective protein, relative to a control sample or a reference standard, indicates that the transplant recipient has an increased risk of delayed graft function, an increased risk of graft rejection, or a poor long-term prognosis.

9. The method of claim 8, wherein the gene that encodes an anti-apoptotic or cytoprotective protein is A20, Bcl-$X_L$, a vascular endothelial growth factor (VEGF), a fibroblast growth factor (FGF), antiopoietin-1, bcl-2, a stress-response gene or gene encoding a heat shock protein, or a member of the IAP gene family (Inhibitors of APoptotis).

10. The method of claim 9, wherein the stress-response gene is heme oxygenase-1 (HO-1).

11. The method of claim 1, the method further comprising assessing a clinical variable known or knowable at the time of the transplantation.

12. The method of claim 11, wherein the clinical variable comprises a variable associated with the donor of the graft, a variable associated with the graft, or a variable associated with the transplant recipient.

13. The method of claim 12, wherein the variable associated with the donor of the graft comprises the donor's age, race, or status as living or deceased; the variable associated with the graft comprises the ischemic time; and the variable associated with the transplant recipient comprises the recipient's age, race, or number of previous grafts the transplant recipient received or attempted to receive.

14. The method of claim 1, wherein the transplant recipient is human.

15. The method of claim 1, wherein the sample is obtained within about 15 minutes after vascular reperfusion is completed.

16. The method of claim 1, wherein the at least one gene is a gene listed in FIG. 5A-5I.

17. A method of treating a patient with an increased risk for delayed graft function, the method comprising:
   (a) providing a test sample from an organ or tissue transplanted into the patient, wherein the sample is obtained during the operation in which the organ or tissue was transplanted and after vascular reperfusion of the organ or tissue;
   (b) determining a level of expression of TNF-α in the test sample, wherein an increased level of expression of TNF-α relative to a control sample or reference standard indicates that the patient has an increased risk for delayed graft function; and
   (c) administering to the patient identified as having an increased risk for delayed graft function an immunosuppressant.

18. The method of claim 17, wherein the method further comprises:
   determining a level of expression of one or more of the following genes: CD25, A20, IL-10, and ICAM-1
   wherein an increased level of expression of the one or more genes relative to a control sample or reference standard indicates that the patient has an increased risk for delayed graft function.

19. A method of assessing a patient's risk for acute graft rejection, the method comprising:
   (a) providing a test sample from an organ or tissue transplanted into the patient, wherein the sample is obtained after vascular reperfusion of the organ or tissue; and
   (b) determining levels of expression of CD3, CD25, and one or more genes selected from the group consisting of TNF-α, IL-6, ICAM-1, HO-1, IFNγ, and CD40 in the test sample;
   wherein increased levels of expression of CD3, CD25, and the one or more genes relative to a control sample or reference standard indicates that the patient has an increased risk for acute graft rejection.

20. The method of claim 19, wherein the method further comprises determining a level of expression of Bcl-$X_L$ in the test sample.

21. The method of claim 17, further comprising assessing a clinical variable known or knowable at the time of the transplantation.

22. The method of claim 21, wherein the clinical variable comprises a variable associated with the donor of the graft, a variable associated with the graft, or a variable associated with the transplant recipient.

23. The method of claim 22, wherein the variable associated with the donor of the graft comprises the donor's age, race, or status as living or deceased; the variable associated with the graft comprises the ischemic time; and the variable associated with the transplant recipient comprises the recipient's age, race, or number of previous grafts the transplant recipient received or attempted to receive.

24. The method of claim 19, wherein the method comprises determining levels of expression of CD3, CD25, and two or more genes selected from the group consisting of TNF-α, IL-6, ICAM-1, HO-1, IFNγ, and CD40 in the test sample.

25. The method of claim 19, wherein the method comprises determining levels of expression of CD3, CD25, and three or more genes selected from the group consisting of TNF-α, IL-6, ICAM-1, HO-1, IFNγ, and CD40 in the test sample.

* * * * *

UNITED STATES PATENT AND TRADEMARK OFFICE
CERTIFICATE OF CORRECTION

PATENT NO. : 8,741,557 B2  
APPLICATION NO. : 10/545198  
DATED : June 3, 2014  
INVENTOR(S) : Terry B. Strom et al.

Page 1 of 1

It is certified that error appears in the above-identified patent and that said Letters Patent is hereby corrected as shown below:

On the Title Page, Item (56), in Col. 2 (Other Publications), line 1, delete "Wiggins eta l.," and insert -- Wiggins et al., --.

In the Claims

In Col. 28, line 19, in Claim 9, delete "APoptotis)." and insert -- APoptosis). --.

Signed and Sealed this
Twelfth Day of August, 2014

Michelle K. Lee
*Deputy Director of the United States Patent and Trademark Office*

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ccctgcccct acatttggag                                              20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ccgggttatg ctggttgtac a                                            21

<210> SEQ ID NO 3
<211> LENGTH: 25
<212> TYPE: DNA
<213> ORGANISM: Artificial Sequence
<220> FEATURE:
<223> OTHER INFORMATION: Probe sequence

<400> SEQUENCE: 3
cacgcagtac agcaaggtcc tggcc                                        25

<210> SEQ ID NO 4
<211> LENGTH: 26
<212> TYPE: DNA
<213> ORGANISM: Artificial Sequence
<220> FEATURE:
<223> OTHER INFORMATION: Primer
```

-continued

```
<400> SEQUENCE: 4
cagatgtagc ggataatgga actctt                                           26

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
gagacaattt ggctctgcat tatttt                                           26

<210> SEQ ID NO 6
<211> LENGTH: 35
<212> TYPE: DNA
<213> ORGANISM: Artificial Sequence
<220> FEATURE:
<223> OTHER INFORMATION: Probe sequence

<400> SEQUENCE: 6
tcactctcct ctttccaatt cttcaaaatg cctaa                                 35

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
aagaaatggg tggtattaca cagaca                                           26

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
tgccatagta tttcagatcc aggat                                            25

<210> SEQ ID NO 9
<211> LENGTH: 33
<212> TYPE: DNA
<213> ORGANISM: Artificial Sequence
<220> FEATURE:
<223> OTHER INFORMATION: Probe sequence

<400> SEQUENCE: 9
ccatctctgg aaccacagta atattgacat gcc                                   33

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
cctcagaatc taccaagagt gaactg                                           26

<210> SEQ ID NO 11
<211> LENGTH: 24
<212> TYPE: DNA
```

```
<213> ORGANISM: Artificial Sequence
<220> FEATURE:
<223> OTHER INFORMATION: Primer

<400> SEQUENCE: 11
acttaatgtg gagctgagct cctt                                              24

<210> SEQ ID NO 12
<211> LENGTH: 26
<212> TYPE: DNA
<213> ORGANISM: Artificial Sequence
<220> FEATURE:
<223> OTHER INFORMATION: Probe sequence

<400> SEQUENCE: 12
caccgtgacg gaatccttct ctacac                                            26

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
cggctgacgt gtgcagtaat ac                                                22

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
cttctgagac ctctggcttc gt                                                22

<210> SEQ ID NO 15
<211> LENGTH: 22
<212> TYPE: DNA
<213> ORGANISM: Artificial Sequence
<220> FEATURE:
<223> OTHER INFORMATION: Probe sequence

<400> SEQUENCE: 15
tctacagctt tccggcgccc aa                                                22

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
ctgcccagga atgctacaga tac                                               23

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ttaacaagtg gaacagctcg gatt                                              24
```

```
<210> SEQ ID NO 18
<211> LENGTH: 27
<212> TYPE: DNA
<213> ORGANISM: Artificial Sequence
<220> FEATURE:
<223> OTHER INFORMATION: Probe Sequence

<400> SEQUENCE: 18
ccattgttct cggctatgac agccatc                                           27
```